US012571028B2

(12) United States Patent
Ma et al.

(10) Patent No.: US 12,571,028 B2
(45) Date of Patent: Mar. 10, 2026

(54) METHODS FOR MULTIPLEX DETECTION OF NUCLEIC ACIDS BY IN SITU HYBRIDIZATION

(71) Applicant: ADVANCED CELL DIAGNOSTICS, INC., Newark, CA (US)

(72) Inventors: Xiao-Jun Ma, Newark, CA (US); Bingqing Zhang, Newark, CA (US); Li-chong Wang, Newark, CA (US); Han Lu, Newark, CA (US); Li Wang, Newark, CA (US); Hailing Zong, Newark, CA (US)

(73) Assignee: ADVANCED CELL DIAGNOSTICS, INC., Newark, CA (US)

( * ) Notice: Subject to any disclaimer, the term of this patent is extended or adjusted under 35 U.S.C. 154(b) by 1184 days.

(21) Appl. No.: 17/430,463

(22) PCT Filed: Feb. 14, 2020

(86) PCT No.: PCT/US2020/018241
§ 371 (c)(1),
(2) Date: Aug. 12, 2021

(87) PCT Pub. No.: WO2020/168162
PCT Pub. Date: Aug. 20, 2020

(65) Prior Publication Data
US 2022/0154262 A1     May 19, 2022

Related U.S. Application Data

(60) Provisional application No. 62/806,574, filed on Feb. 15, 2019.

(51) Int. Cl.
*C12Q 1/68* (2018.01)
*C12Q 1/6818* (2018.01)
*C12Q 1/682* (2018.01)
*C12Q 1/6841* (2018.01)
*C12Q 1/6876* (2018.01)

(52) U.S. Cl.
CPC ......... *C12Q 1/6841* (2013.01); *C12Q 1/6818* (2013.01); *C12Q 1/682* (2013.01); *C12Q 1/6876* (2013.01)

(58) Field of Classification Search
CPC ....................................................... C12Q 1/68
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Wilhelmus et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,124,246 A | 6/1992 | Urdea et al. | |
| 5,635,352 A | 6/1997 | Urdea et al. | |
| 5,681,697 A | 10/1997 | Urdea et al. | |
| 5,710,264 A | 1/1998 | Urdea et al. | |
| 5,849,481 A | 12/1998 | Urdea et al. | |
| 6,465,175 B2 | 10/2002 | Horn et al. | |
| 7,399,845 B2 | 7/2008 | Seth et al. | |
| 7,709,198 B2* | 5/2010 | Luo ..................... | C12Q 1/6841 536/23.1 |
| 8,658,361 B2* | 2/2014 | Wu ..................... | C12Q 1/6841 422/82.07 |
| 9,315,854 B2 | 4/2016 | Wu et al. | |
| 2007/0015188 A1 | 1/2007 | Luo et al. | |
| 2008/0038725 A1 | 2/2008 | Luo et al. | |
| 2009/0081688 A1 | 3/2009 | Luo et al. | |
| 2012/0100540 A1 | 4/2012 | Wu et al. | |
| 2016/0046984 A1 | 2/2016 | Nguyen et al. | |
| 2016/0201117 A1 | 7/2016 | Wu et al. | |
| 2017/0101672 A1 | 4/2017 | Luo et al. | |
| 2018/0030504 A1 | 2/2018 | Nolan et al. | |
| 2018/0094305 A1 | 4/2018 | Sternson et al. | |

(Continued)

FOREIGN PATENT DOCUMENTS

| | | |
|---|---|---|
| CN | 114945681 A | 8/2022 |
| WO | WO 2007/001986 | 1/2007 |
| WO | WO 2007/002006 | 1/2007 |

(Continued)

OTHER PUBLICATIONS

Anderson et al., 2016. Fully automated RNAscope in situ hybridization assays for formalin-fixed paraffin-embedded cells and tissues. Journal of cellular biochemistry, 117(10), pp. 2201-2208. (Year: 2016).*

Moffitt1 et al., 2016. High-throughput single-cell gene-expression profiling with multiplexed error-robust fluorescence in situ hybridization. P.N.A.S., 113(39), pp. 11046-11051. (Year: 2016).*

Mondal et al., 2018. Highly multiplexed single-cell in situ RNA and DNA analysis with bioorthogonal cleavable fluorescent oligonucleotides. Chemical Science, 9(11), pp. 2909-2917. (Year: 2018).*

Moffitt2 et al., 2016. High-performance multiplexed fluorescence in situ hybridization in culture and tissue with matrix imprinting and clearing. P.N.A.S., 113(50), pp. 14456-14461. (Year: 2016).*

(Continued)

*Primary Examiner* — Gary Benzion
*Assistant Examiner* — Olayinka A Oyeyemi
(74) *Attorney, Agent, or Firm* — Casimir Jones, S.C.; Peter J. Schlueter

(57) ABSTRACT

The invention relates to methods of multiplex detection of a plurality of target nucleic acids by contacting a sample comprising a cell with target probe sets that specifically hybridize to target nucleic acids, with pre-amplifiers or pre-pre-amplifiers specific for each target probe set, with amplifiers specific for the pre-amplifiers, and with label probes specific for the amplifiers, resulting in specific labeling of multiple target nucleic acids. The invention also relates to samples, slides and kits relating to detection of multiple target nucleic acids.

9 Claims, 10 Drawing Sheets

Specification includes a Sequence Listing.

(56) References Cited

U.S. PATENT DOCUMENTS

2023/0002815 A1* 1/2023 Wang .................. C12Q 1/6841

FOREIGN PATENT DOCUMENTS

| WO | WO 2011/038403 | | 3/2011 | | |
| WO | WO 2012/054795 | | 4/2012 | | |
| WO | WO 2017/066211 | | 4/2017 | | |
| WO | WO 2018/089438 | | 5/2018 | | |
| WO | WO-2020092796 | A1 * | 5/2020 | ............ | C12Q 1/682 |
| WO | WO-2021102337 | A1 * | 5/2021 | ..... | A61K 39/001112 |
| WO | WO-2024124041 | A1 * | 6/2024 | ............ | C12Q 1/682 |

OTHER PUBLICATIONS

Wang et al., "Multiplexed imaging of high-density libraries of RNAs with MERFISH and expansion microscopy" Scientific Reports 2018, 8:4847, 13 pages.

Wang et al., "a novel in situ RNA analysis platform for formalin-fixed, paraffin-embedded tissues" J. Molecular Diagnostics, Jan. 2012, 14(1): 22-29.

International Search Report and Written Opinion for PCT/US20/18241. Mailed Jul. 14, 2020. 21 pages.

Anderson et al., Fully Automated RNAscope In Situ Hybridization Assays for Formalin-Fixed Paraffin-Embedded Cells and Tissues. J Cell Biochem. Oct. 2016;117(10):2201-8.

Ausubel et al., Current Protocols in Molecular Biology, John Wiley and Sons, Baltimore, MD. 1999. TOC only. 3 pages.

Baker et al., Robust RNA-based in situ mutation detection delineates colorectal cancer subclonal evolution. Nat Commun. Dec. 8, 2017;8(1):1998. 8 pages.

Baxter et al., Multiparametric characterization of rare HIV-infected cells using an RNA-flow FISH technique. Nat Protoc. Oct. 2017;12(10):2029-2049.

Brown et al., New technologies for cervical cancer screening. Best Pract Res Clin Obstet Gynaecol. Apr. 2012;26(2):233-42.

Cecil Textbook of Medicine, Bennett and Plum, eds., 20th ed., WB Saunders, Philadelphia. 1996. TOC only. 42 pages.

Cervical Cytology Practice Guidelines TOC, Approved by the American Society of Cytopathology (ASC) Executive Board, Nov. 10, 2000. 26 pages.

Choi et al., Third-generation in situ hybridization chain reaction: multiplexed, quantitative, sensitive, versatile, robust. Development 145(12), pii: dev165753. 2018. 10 pages.

Codeluppi et al., Spatial organization of the somatosensory cortex revealed by osmFISH. Nat Methods. Nov. 2018;15(11):932-935.

Colposcopy and Treatment of Cervical Intraepithelial Neoplasia: A Beginner's Manual, Sellors and Sankaranarayanan, eds., International Agency for Research on Cancer, Lyon, France. 2003. TOC only. 3 pages.

Daniel et al., FastTag Nucleic Acid Labeling System: a versatile method for incorporating haptens, fluorochromes and affinity ligands into DNA, RNA and oligonucleotides. Biotechniques. Mar. 1998;24(3):484-9.

Dey, "Cytology Sample Procurement, Fixation and Processing" in Basic and Advanced Laboratory Techniques in Histopathology and Cytology. Springer, Singapore. 2018. pp. 121-132.

Hanley et al., Detection of low abundance RNA molecules in individual cells by flow cytometry. PLoS One. 2013;8(2):e57002. 8 pages.

Hermanson, Bioconjugate Techniques, Academic Press, San Diego. 1996. TOC only. 2 pages.

Hicks et al., In situ hybridization in the pathology laboratory: general principles, automation, and emerging research applications for tissue-based studies of gene expression. J Mol Histol. Aug. 2004;35(6):595-601.

Hu et al., Fluorescence in situ hybridization (FISH): an increasingly demanded tool for biomarker research and personalized medicine. Biomark Res. Feb. 5, 2014;2(1):3. 13 pages.

Johnson et al., Molecular Probes Handbook, a Guide to Fluorescent Probes and Labeling Technologies, 11th ed., Life Technologies. 2010. TOC only. 2 pages.

Kalof et al., Our approach to squamous intraepithelial lesions of the uterine cervix. J Clin Pathol. May 2007;60(5):449-55.

Kishi et al., SABER amplifies FISH: enhanced multiplexed imaging of RNA and DNA in cells and tissues. Nat Methods. Jun. 2019;16(6):533-544.

Larsson et al., In situ detection and genotyping of individual mRNA molecules. Nat Methods. May 2010;7(5):395-7.

Lowe. Distinctive Image Features from Scale-Invariant Keypoints. Internat. J. Computer Vision 60(2) 2004: 91-110.

Majlessi et al., Advantages of 2'-O-methyl oligoribonucleotide probes for detecting RNA targets. Nucleic Acids Res. May 1, 1998;26(9):2224-9.

Manafi et al., Fluorogenic and chromogenic substrates used in bacterial diagnostics. Microbiol Rev. Sep. 1991;55(3):335-48.

Moffitt et al., High-throughput single-cell gene-expression profiling with multiplexed error-robust fluorescence in situ hybridization. Proc Natl Acad Sci U S A. Sep. 27, 2016;113(39):11046-51.

Petersen et al., LNA: a versatile tool for therapeutics and genomics. Trends Biotechnol. Feb. 2003;21(2):74-81.

Ratan et al., Application of Fluorescence In Situ Hybridization (FISH) Technique for the Detection of Genetic Aberration in Medical Science. Cureus. Jun. 9, 2017;9(6):e1325. 13 pages.

Rouhanifard et al., Exponential fluorescent amplification of individual RNAs using clampFISH probes BioRxiv, 222794. 2018. 17 pages.

Sambrook et al., Molecular Cloning: A Laboratory Manual, Third Ed., Cold Spring Harbor Laboratory, New York. 2001. TOC only. 23 pages.

Santalucia, A unified view of polymer, dumbbell, and oligonucleotide DNA nearest-neighbor thermodynamics. Proc Natl Acad Sci U S A. Feb. 17, 1998;95(4):1460-5.

Schindelin et al., The ImageJ ecosystem: An open platform for biomedical image analysis. Mol Reprod Dev. Jul.-Aug. 2015;82(7-8):518-29.

Schneider et al., NIH Image to ImageJ: 25 years of image analysis. Nat Methods. Jul. 2012;9(7):671-5.

Schulz et al., Simultaneous Multiplexed Imaging of mRNA and Proteins with Subcellular Resolution in Breast Cancer Tissue Samples by Mass Cytometry. Cell Syst. Jan. 24, 20184;6(1):25-36.e5. 6 pages.

Shah et al., In Situ Transcription Profiling of Single Cells Reveals Spatial Organization of Cells in the Mouse Hippocampus. Neuron. Oct. 19, 2016;92(2):342-357.

Sidorenko et al., Correlated cleavage of single- and double-stranded substrates by uracil-DNA glycosylase. FEBS Lett. Feb. 6, 2008;582(3):410-4.

Stoler, In situ hybridization. Clin Lab Med. Mar. 1990;10(1):215-36.

Wang et al., Characterization of denaturation and renaturation of DNA for DNA hybridization. Environ Health Toxicol. Sep. 11, 2014;29:e2014007.

Wang et al., RNAscope: a novel in situ RNA analysis platform for formalin-fixed, paraffin-embedded tissues. J Mol Diagn. Jan. 2012;14(1):22-9.

Waxman et al., Revised terminology for cervical histopathology and its implications for management of high-grade squamous intraepithelial lesions of the cervix. Obstet Gynecol. Dec. 2012;120(6):1465-71.

Weier et al., FISH in cancer diagnosis and prognostication: from cause to course of disease. Expert Rev Mol Diagn. Mar. 2002;2(2):109-19.

Wilkinson, ed. In situ hybridization. A practical approach. IRL Press, Oxford. 1992. TOC only. 8 pages.

Yang et al., Artificially expanded genetic information system: a new base pair with an alternative hydrogen bonding pattern. Nucleic Acids Res. 2006;34(21):6095-101.

Extended European Search Report for European Application No. 20755307.4, mailed Oct. 26, 2022, 9 Pages.

* cited by examiner

Target 12

Target 1

Amplification system

Double Z Probe

- Simultaneous target probe hybridization and signal amplification

- Iterative detection and imaging

SEQUENCE LISTING

<160> NUMBER OF SEQ ID NOS: 5

<210> SEQ ID NO 1
<211> LENGTH: 8
<212> TYPE: PRT

-continued

```
<213> ORGANISM: Unknown
<220> FEATURE:
<223> OTHER INFORMATION: Description of Unknown:
      Cleavage site sequence of Human rhinovirus 3C protease

<400> SEQUENCE: 1

Leu Glu Val Leu Phe Gln Gly Pro
1               5

<210> SEQ ID NO 2
<211> LENGTH: 5
<212> TYPE: PRT
<213> ORGANISM: Unknown
<220> FEATURE:
<223> OTHER INFORMATION: Description of Unknown:
      Cleavage site sequence of enterokinase

<400> SEQUENCE: 2

Asp Asp Asp Asp Lys
1               5

<210> SEQ ID NO 3
<211> LENGTH: 4
<212> TYPE: PRT
<213> ORGANISM: Unknown
<220> FEATURE:
<223> OTHER INFORMATION: Description of Unknown:
      Cleavage site sequence of factor Xa

<400> SEQUENCE: 3

Ile Glu Gly Arg
1

<210> SEQ ID NO 4
<211> LENGTH: 7
<212> TYPE: PRT
<213> ORGANISM: Unknown
<220> FEATURE:
<223> OTHER INFORMATION: Description of Unknown:
      Cleavage site sequence of Tobacco etch virus protease

<400> SEQUENCE: 4

Glu Asn Leu Tyr Phe Gln Gly
1               5

<210> SEQ ID NO 5
<211> LENGTH: 6
<212> TYPE: PRT
<213> ORGANISM: Unknown
<220> FEATURE:
<223> OTHER INFORMATION: Description of Unknown:
      Cleavage site sequence of thrombin

<400> SEQUENCE: 5

Leu Val Pro Arg Gly Ser
1               5
```

METHODS FOR MULTIPLEX DETECTION OF NUCLEIC ACIDS BY IN SITU HYBRIDIZATION

CROSS REFERENCE TO RELATED APPLICATION

This application is a national phase application under 35 U.S.C. § 371 of PCT International Application No. PCT/US2020/018241, filed Feb. 14, 2020, which claims the benefit of U.S. Provisional application No. 62/806,574 filed Feb. 15, 2019, the entire contents of both of which are incorporated herein by reference in their entirety for all purposes.

SEQUENCE LISTING

This application incorporates herein by reference a Sequence Listing as an ASCII text file entitled "38636-252_Sequence_Listing.txt" created on Aug. 3, 2021, and having a size of 1,348 bytes. The Sequence Listing contained in this .txt file is part of the specification, and is hereby incorporated by reference herein in its entirety.

BACKGROUND OF THE INVENTION

The present invention relates generally to detection of nucleic acids, and more specifically to multiplex detection of nucleic acids.

RNA in situ hybridization (ISH) is a molecular biology technique widely used to measure and localize specific RNA sequences, for example, messenger RNAs (mRNAs), long non-coding RNAs (lncRNAs), and microRNAs (miRNAs) within cells, such as circulating tumor cells (CTCs) or tissue sections, while preserving the cellular and tissue context. RNA ISH therefore provides for spatial-temporal visualization as well as quantification of gene expression within cells and tissues. It has wide applications in research and in diagnostics (Hu et al., *Biomark. Res.* 2(1):1-13, doi: 10.1186/2050-7771-2-3 (2014); Ratan et al., *Cureus* 9(6): e1325. doi: 10.7759/cureus.1325 (2017); Weier et al., *Expert Rev. Mol. Diagn.* 2(2):109-119 (2002)). Fluorescent RNA ISH utilizes fluorescent dyes and fluorescent microscopes for RNA labeling and detection, respectively. Fluorescent RNA ISH typically provides for limited multiplexing of four to five target sequences. The limited multiplexing capability is largely due to the small number of spectrally distinct fluorescent dyes that can be distinguished by the optical systems of the fluorescence microscope. Higher level of multiplexing is highly desirable in areas such as generating cell and tissue maps to understand complex biological systems, particularly in human health and disease.

Several approaches have been introduced that utilize serial rounds of hybridization, imaging, removal of labels and re-hybridization to distinct targets, which in theory provides for imaging of multiples of four to five targets in the same cell or tissue section (Shah et al., *Neuron* 92(2): 342-357 (2016); Codeluppi et al., *Nature Methods* 15(11): 932-935 (2018)). In practice, however, the previously described sequential fluorescent ISH (FISH) method can result in substantial loss of nucleic acid detection sensitivity, in particular RNA detection sensitivity, and cellular morphology in successive rounds of hybridization and detection. In addition, the method is time and labor intensive due to the need to repeat the entire target probe hybridization and label detection steps. Therefore, a more practical and sensitive method that allows simultaneous visualization of a higher number of target sequences remains a technical challenge.

Thus, there exists a need for in situ detection methods for multiplex detection of higher numbers of target nucleic acids. The present invention satisfies this need and provides related advantages as well.

SUMMARY OF INVENTION

The invention provides a method of detecting a plurality of target nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier; (C) contacting the sample with a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe; (D) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes specifically label a first subset of target nucleic acids hybridized to the plurality of target probe sets; (E) detecting the label probes of the first set of label probes bound to the target nucleic acids, thereby detecting the first subset of target nucleic acids; (F) cleaving the labels from the first set of label probes bound to the first subset of target nucleic acids; (G) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes specifically label a second subset of target nucleic acids hybridized to the plurality of target probe sets that is different than the first subset of target nucleic acids; and (H) detecting the label probes of the second set of label probes bound to the target nucleic acids, thereby detecting the second subset of target nucleic acids, wherein a plurality of target nucleic acids are detected.

In one embodiment, the method further comprises (I) cleaving the labels from the second set of label probes bound to the second set of target nucleic acids; (J) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes specifically label a third subset of target nucleic acids hybridized to the plurality of target probe sets that is different than the first and second subsets of target nucleic acids; and (K) detecting the label probes of the third set of label probes bound to the target nucleic acids, thereby detecting the third subset of target nucleic acids. In one embodiment, the method comprises repeating steps (I) through (K) one or more times.

In one embodiment, each target probe set comprises two or more pairs of target probes that specifically hybridize to the same target nucleic acid.

In one embodiment, the target nucleic acids are independently DNA or RNA. In a particular embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a method, the sample is a tissue specimen or is derived from a tissue specimen. In one embodiment of such a method, the sample is a blood sample or is derived from a blood sample. In one embodiment of such a method, the sample is a cytological sample or is derived from a cytological sample.

The invention additionally provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier, wherein the pre-amplifiers are hybridized to the respective specific target probe pairs; (D) a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe, wherein the amplifiers are hybridized to the respective pre-amplifiers specific for the target probe sets; (E) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets, wherein the hybridizations provide a detectable label on the first subset of target nucleic acids.

In one embodiment, the labels of the first set of label probes bound to the first subset of target nucleic acids are cleaved.

In one embodiment of such a sample, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are cleaved.

In one embodiment of such a sample of the invention, a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment of a sample of the invention, the target nucleic acids are independently DNA or RNA. In some embodiments, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of a sample of the invention, the sample is a tissue specimen or is derived from a tissue specimen. In one embodiment of a sample of the invention, the sample is a blood sample or is derived from a blood sample. In one embodiment of a sample of the invention, the sample is a cytological sample or is derived from a cytological sample.

The invention additionally provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier, wherein the pre-amplifiers are hybridized to the respective specific target probe pairs; (D) a set of amplifiers, wherein the set of amplifiers comprises a plurality of subsets of amplifiers specific for each preamplifier, wherein each subset of amplifiers comprises a plurality of amplifiers, wherein the amplifiers of a subset of amplifiers comprise a binding site for one of the preamplifiers specific for a target probe set and a plurality of binding sites for a label probe, wherein the amplifiers are hybridized to the respective pre-amplifiers specific for the target probe sets; (E) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets, wherein the hybridizations provide a detectable label on the first subset of target nucleic acids.

In one embodiment, the labels of the first set of label probes bound to the first subset of target nucleic acids are cleaved.

In one embodiment of a slide of the invention, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are cleaved.

In one embodiment of a slide of the invention, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment of such a slide, each target probe set comprises two or more pairs of target probes that specifically hybridize to the same target nucleic acid.

In one embodiment of such a slide, the target nucleic acids are independently DNA or RNA. In some embodiments, the target nucleic acids that are RNA are independently selected from the group consisting of messenger RNA (mRNA), micro RNA (miRNA), ribosomal RNA (rRNA), mitochondrial RNA, and non-coding RNA.

In some embodiments of a slide of the invention, the sample is a tissue specimen or is derived from a tissue specimen. In some embodiments of a slide of the invention, the sample is a blood sample or is derived from a blood sample. In some embodiments of a slide of the invention, the sample is a cytological sample or is derived from a cytological sample.

In another embodiment, the invention provides a kit for in situ detection of target nucleic acids, comprising (A) a set of pre-amplifiers, wherein the set of pre-amplifiers comprises a plurality of pre-amplifiers, wherein the plurality of preamplifiers comprises a pre-amplifier specific for each target probe set, wherein each pre-amplifier comprises binding sites for the pair of target probes of one of the target probe sets and a plurality of binding sites for an amplifier; (B) a set of amplifiers, wherein the set of amplifiers comprises a plurality of subsets of amplifiers specific for each preamplifier, wherein each subset of amplifiers comprises a plurality of amplifiers, wherein the amplifiers of a subset of amplifiers comprise a binding site for one of the preamplifiers specific for a target probe set and a plurality of binding sites for a label probe; (C) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes can specifically label a first subset of target nucleic acids; (D) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes can specifically label a second subset of target nucleic acids that is different than the first subset of target nucleic acids.

In one embodiment, the kit further comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes can specifically label a third subset of target nucleic acids that is different than the first and second subsets of target nucleic acids.

In one embodiment of such a kit, the kit comprises one or more target probe sets, wherein each target probe set comprises a pair of target probes that specifically hybridize to a target nucleic acid. In one embodiment of such a kit, each target probe set comprises two or more pairs of target probes that can specifically hybridize to the same target nucleic acid. In one embodiment of such a kit, the kit comprises a cleaving agent to cleave the cleavable labels from the label probes. In one embodiment of such a kit, the kit comprises at least one reagent for permeabilizing cells.

In another embodiment, the invention provides a method of detecting a plurality of nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier; (C) contacting the sample with a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier; (D) contacting the sample with a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe; (E) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes specifically label a first subset of target nucleic acids hybridized to the plurality of target probe sets; (F) detecting the label probes of the first set of label probes bound to the target nucleic acids, thereby detecting the first subset of target nucleic acids; (G) cleaving the labels from the first set of label probes bound to the first subset of target nucleic acids; (H) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes specifically label a second subset of target nucleic acids hybridized to the plurality of target probe sets that is different than the first subset of target nucleic acids; and (I) detecting the label probes of the second set of label probes bound to the target nucleic acids, thereby detecting the second subset of target nucleic acids, wherein a plurality of target nucleic acids are detected.

In one embodiment, the method further comprises (J) cleaving the labels from the second set of label probes bound to the second set of target nucleic acids; (K) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes specifically label a third subset of target nucleic acids hybridized to the plurality of target probe sets that is different than the first and second subsets of target nucleic acids; and (L) detecting the label probes of the third set of label probes bound to the target nucleic acids, thereby detecting the third subset of target nucleic acids. In one embodiment, steps (J) through (L) are repeated one or more times.

In one embodiment of such a method, each target probe set comprises two or more pairs of target probes that specifically hybridize to the same target nucleic acid.

In one embodiment of such a method, the target nucleic acids are independently DNA or RNA. In some embodiments, the target nucleic acids that are RNA are independently selected from the group consisting of messenger RNA (mRNA), micro RNA (miRNA), ribosomal RNA (rRNA), mitochondrial RNA, and non-coding RNA.

In some embodiments of a method of the invention, the sample is a tissue specimen or is derived from a tissue specimen. In some embodiments of a method of the invention, the sample is a blood sample or is derived from a blood sample. In some embodiments of a method of the invention, the sample is a cytological sample or is derived from a cytological sample.

In another embodiment, the invention provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier, wherein the pre-pre-amplifiers are hybridized to the respective specific target probe pairs; (D) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier, wherein the pre-amplifiers are hybridized to the respective pairs of pre-pre-amplifiers; (E) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets, wherein the hybridizations provide a detectable label on the first subset of target nucleic acids.

In one embodiment, the labels of the first set of label probes bound to the first subset of target nucleic acids are cleaved.

In one embodiment of such a sample of the invention, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids; and wherein the hybridizations provide a detectable label on the second subset of target nucleic acids.

In one embodiment, the labels from the second set of label probes bound to the second subset of target nucleic acids are cleaved.

In one embodiment of such a sample of the invention, the sample comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment of such a sample, each target probe set comprises two or more pairs of target probes that specifically hybridize to the same target nucleic acid.

In one embodiment of such a sample, the target nucleic acids are independently DNA or RNA. In some embodiments of such a sample, the target nucleic acids that are RNA are independently selected from the group consisting of messenger RNA (mRNA), micro RNA (miRNA), ribosomal RNA (rRNA), mitochondrial RNA, and non-coding RNA.

In some embodiments of a sample of the invention, the sample is a tissue specimen or is derived from a tissue specimen. In some embodiments of a sample of the invention, the sample is a blood sample or is derived from a blood sample. In some embodiments of a sample of the invention, the sample is a cytological sample or is derived from a cytological sample.

The invention additionally provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier, wherein the pre-pre-amplifiers are hybridized to the respective specific target probe pairs; (D) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier, wherein the pre-amplifiers are hybridized to the respective pairs of pre-pre-amplifiers; (E) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets, wherein the hybridizations provide a detectable label on the first subset of target nucleic acids.

In one embodiment, the labels of the first set of label probes bound to the first subset of target nucleic acids are cleaved.

In one embodiment of such a slide, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids; and wherein the hybridizations provide a detectable label on the second subset of target nucleic acids.

In one embodiment, the labels from the second set of label probes bound to the second subset of target nucleic acids are cleaved.

In one embodiment of such a slide, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment of such a slide, each target probe set comprises two or more pairs of target probes that specifically hybridize to the same target nucleic acid.

In one embodiment of such a slide, the target nucleic acids are independently DNA or RNA. In some embodiments, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a slide, the sample is a tissue specimen or is derived from a tissue specimen. In one embodiment of such a slide, the sample is a blood sample or is derived from a blood sample. In one embodiment of such a slide, the sample is a cytological sample or is derived from a cytological sample.

In another embodiment, the invention provides a kit for in situ detection of target nucleic acids, comprising (A) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier; (B) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier; (C) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe; (D) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes can specifically label a first subset of target nucleic acids; (E) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes can specifically label a second subset of target nucleic acids that is different than the first subset of target nucleic acids; and.

In one embodiment of such a kit, the kit comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes can specifically label a third subset of target nucleic acids that is different than the first and second subsets of target nucleic acids In one embodiment of such a kit, the kit comprises one or more target probe sets, wherein each target probe set comprises a pair of target probes that specifically hybridize to a target nucleic acid. In one embodiment of such a kit, each target probe set comprises two or more pairs of target probes that can specifically hybridize to the same target nucleic acid.

In one embodiment of such a kit, the kit comprises a cleaving agent to cleave the cleavable labels from the label probes. In one embodiment, the kit comprises at least one reagent for permeabilizing cells.

In one embodiment, the invention provides a method of detecting a plurality of target nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier; (C) contacting the sample with a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier; (D) contacting the sample with a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe; (E) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes specifically label a first subset of target nucleic acids hybridized to the plurality of target probe sets; (F) detecting the label probes of the first set of label probes bound to the target nucleic acids, thereby detecting the first subset of target nucleic acids; (G) cleaving the labels from the first set of label probes bound to the first subset of target nucleic acids; (H) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes specifically label a second subset of target nucleic acids hybridized to the plurality of target probe sets that is different than the first subset of target nucleic acids; and (I) detecting the label probes of the second set of label probes bound to the target nucleic acids, thereby detecting the second subset of target nucleic acids; wherein a plurality of target nucleic acids are detected.

In one embodiment of such a method, the method further comprises (J) cleaving the labels from the second set of label probes bound to the second set of target nucleic acids; (K) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes specifically label a third subset of target nucleic acids hybridized to the plurality of target probe sets that is different than the first and second subsets of target nucleic acids; and (L) detecting the label probes of the third set of label probes bound to the target nucleic acids, thereby detecting the third subset of target nucleic acids. In one embodiment of such a method, the method comprises repeating steps (J) through (L) one or more times.

In one embodiment of such a method, each target probe set comprises two or more pairs of target probes that specifically hybridize to the same target nucleic acid.

In one embodiment of such a method, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a method, the sample is a tissue specimen or is derived from a tissue specimen. In another embodiment, the sample is a blood sample or is derived from a blood sample. In yet another embodiment, the sample is a cytological sample or is derived from a cytological sample.

In one embodiment, the invention provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier, wherein the pre-pre-amplifiers are hybridized to the respective specific target probe pairs; (D) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier, wherein the pre-amplifiers are hybridized to the respective pre-pre-amplifiers specific for the target probe sets; (E) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment of such a sample, the labels of the first set of label probes bound to the first subset of target nucleic acids are cleaved.

In one embodiment of such a sample, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment of such a sample, the labels from the second set of label probes bound to the second subset of target nucleic acids are cleaved.

In one embodiment of such a sample, the sample comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment of such a sample, each target probe set comprises two or more pairs of target probes that specifically hybridize to the same target nucleic acid.

In one embodiment of such a sample, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a sample, the sample is a tissue specimen or is derived from a tissue specimen. In another embodiment of such a sample, the sample is a blood sample or is derived from a blood sample. In yet another embodiment, the sample is a cytological sample or is derived from a cytological sample.

In one embodiment, the invention provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier, wherein the pre-pre-amplifiers are hybridized to the respective specific target probe pairs; (D) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier, wherein the pre-amplifiers are hybridized to the respective pre-pre-amplifiers specific for the target probe sets; (E) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment of such a slide, the labels of the first set of label probes bound to the first subset of target nucleic acids are cleaved.

In one embodiment of such a slide, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment of such a slide, the labels from the second set of label probes bound to the second subset of target nucleic acids are cleaved.

In one embodiment of such a slide, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment of such a slide, each target probe set comprises two or more pairs of target probes that specifically hybridize to the same target nucleic acid.

In one embodiment of such a slide, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a slide, the sample is a tissue specimen or is derived from a tissue specimen. In another embodiment of such a slide, the sample is a blood sample or is derived from a blood sample. In yet another embodiment, the sample is a cytological sample or is derived from a cytological sample.

In one embodiment, the invention provides kit for in situ detection of target nucleic acids, comprising (A) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier; (B) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier; (C) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe; (D) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes can specifically label a first subset of target nucleic acids; (E) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes can specifically label a second subset of target nucleic acids that is different than the first subset of target nucleic acids.

In one embodiment of such a kit, the kit further comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes can specifically label a third subset of target nucleic acids that is different than the first and second subsets of target nucleic acids.

In one embodiment of such a kit, the kit comprises one or more target probe sets, wherein each target probe set comprises a pair of target probes that specifically hybridize to a target nucleic acid.

In one embodiment of such a kit, each target probe set comprises two or more pairs of target probes that can specifically hybridize to the same target nucleic acid.

In one embodiment of such a kit, the kit comprises a cleaving agent to cleave the cleavable labels from the label probes. In one embodiment of such a kit, the kit comprises at least one reagent for permeabilizing cells.

In one embodiment, the invention provides a method of detecting a plurality of target nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier; (C) contacting the sample with a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the preamplifiers specific for a target probe set and a plurality of binding sites for a label probe; (D) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-amplifiers and amplifiers, and wherein the first set of label probes specifically label a first subset of target nucleic acids hybridized to the plurality of target probe sets; (E) detecting the label probes of the first set of label probes bound to the target nucleic acids, thereby detecting the first subset of target nucleic acids; (F) incubating the sample at a temperature above the melting temperature between the label probes and amplifiers and lower than the melting temperature between the target probes, pre-amplifiers and amplifiers, thereby removing the labels from the first set of label probes bound to the first subset of target nucleic acids; (G) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-amplifiers and amplifiers, and wherein the second set of label probes specifically label a second subset of target nucleic acids hybridized to the plurality of target probe sets that is different than the first subset of target nucleic acids; and (H) detecting the label probes of the second set of label probes bound to the target nucleic acids, thereby detecting the second subset of target nucleic acids; wherein a plurality of target nucleic acids are detected.

In one embodiment, the method further comprises (I) incubating the sample at a temperature above the melting temperature between the label probes and amplifiers and lower than the melting temperature between the target probes, pre-amplifiers and amplifiers, thereby removing the labels from the second set of label probes bound to the second set of target nucleic acids; (J) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-amplifiers and amplifiers, and wherein the third set of label probes specifically label a third subset of target nucleic acids hybridized to the plurality of target probe sets that is different than the first and second subsets of target nucleic acids; and (K) detecting the label probes of the third set of label probes bound to the target nucleic acids, thereby detecting the third subset of target nucleic acids. In one embodiment, the method comprises repeating steps (I) through (K) one or more times.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a method, the sample is a tissue specimen or is derived from a tissue specimen. In one embodiment, the sample is a blood sample or is derived from a blood sample. In one embodiment, the sample is a cytological sample or is derived from a cytological sample.

The invention additionally provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier, wherein the pre-amplifiers are hybridized to the respective specific target probe pairs; (D) a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe, wherein the amplifiers are hybridized to the respective pre-amplifiers specific for the target probe sets; (E) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-amplifiers and amplifiers.

In one embodiment of such a sample, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-amplifiers and amplifiers, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-amplifiers and amplifiers.

In one embodiment of such a sample of the invention, a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of a sample of the invention, the sample is a tissue specimen or is derived from a tissue specimen. In one embodiment, the sample is a blood sample or is derived from a blood sample. In one embodiment, the sample is a cytological sample or is derived from a cytological sample.

The invention additionally provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier, wherein the pre-amplifiers are hybridized to the respective specific target probe pairs; (D) a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe, wherein the amplifiers are hybridized to the respective pre-amplifiers specific for the target probe sets; (E) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-amplifiers and amplifiers, thereby removing the labels.

In one embodiment, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-amplifiers and amplifiers, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-amplifiers and amplifiers, thereby removing.

In one embodiment, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment of such a slide, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment of such a slide, the sample is a tissue specimen or is derived from a tissue specimen. In one embodiment, the sample is a blood sample or is derived from a blood sample. In one embodiment, the sample is a cytological sample or is derived from a cytological sample.

The invention also provides a kit for in situ detection of target nucleic acids, comprising (A) a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier; (B) a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe; (C) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-amplifiers and amplifiers, and wherein the first set of label probes can specifically label a first subset of target nucleic acids; (D) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-amplifiers and amplifiers, and wherein the second set of label probes can specifically label a second subset of target nucleic acids that is different than the first subset of target nucleic acids.

In one embodiment, the kit comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-amplifiers and amplifiers, and wherein the third set of label probes can specifically label a third subset of target nucleic acids that is different than the first and second subsets of target nucleic acids.

In one embodiment, the kit comprises one or more target probe sets, wherein each target probe set comprises a pair of target probes that specifically hybridize to a target nucleic acid. In one embodiment, each target probe set comprises two or more pairs of target probes that can specifically hybridize to the same target nucleic acid.

In one embodiment, the kit comprises at least one reagent for permeabilizing cells.

The invention also provides a method of detecting a plurality of nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier; (C) contacting the sample with a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier; (D) contacting the sample with a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe; (E) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes specifically label a first subset of target nucleic acids hybridized to the plurality of target probe sets; (F) detecting the label probes of the first set of label probes bound to the target nucleic acids, thereby detecting the first subset of target nucleic acids; (G) incubating the sample at a temperature above the melting temperature between the label probes and amplifiers and lower than the melting temperature between the target probes, pre-pre-amplifiers, pre-amplifiers and amplifiers, thereby removing the labels from the first set of label probes bound to the first subset of target nucleic acids; (H) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes specifically label a second subset of target nucleic acids hybridized to the plurality of target probe sets that is different than the first subset of target nucleic acids; and (I) detecting the label probes of the second set of label probes bound to the target nucleic acids, thereby detecting the second subset of target nucleic acids; wherein a plurality of target nucleic acids are detected.

In one embodiment, the method further comprises (J) incubating the sample at a temperature above the melting temperature between the label probes and amplifiers and lower than the melting temperature between the target probes, pre-pre-amplifiers, pre-amplifiers and amplifiers, thereby removing the labels from the second set of label probes bound to the second set of target nucleic acids; (K) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes specifically label a third subset of target nucleic acids hybridized to the plurality of target probe sets that is different than the first and second subsets of target nucleic acids; and (L) detecting the label probes of the third set of label probes bound to the target nucleic acids, thereby detecting the third subset of target nucleic acids.

In one embodiment, the method comprises repeating steps (J) through (L) one or more times.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample. In one embodiment, the sample is a cytological sample or is derived from a cytological sample.

The invention also provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier, wherein the pre-pre-amplifiers are hybridized to the respective specific target probe pairs; (D) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier, wherein the pre-amplifiers are hybridized to the respective pairs of pre-pre-amplifiers; (E) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes are hybridized to the respective amplifiers and specifically label a second subset of target nucleic acids hybridized to the plurality of target probe sets that is different than the first subset of target nucleic acids; and wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the sample comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample. In one embodiment, the sample is a cytological sample or is derived from a cytological sample.

The invention also provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier, wherein the pre-pre-amplifiers are hybridized to the respective specific target probe pairs; (D) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier, wherein the pre-amplifiers are hybridized to the respective pairs of pre-pre-amplifiers; (E) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes are hybridized to the respective amplifiers and specifically label a second subset of target nucleic acids hybridized to the plurality of target probe sets that is different than the first subset of target nucleic acids; and wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment of such a slide, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample. In one embodiment, the sample is a cytological sample or is derived from a cytological sample.

The invention additionally provides a kit for in situ detection of target nucleic acids, comprising (A) a set of pre-pre-amplifiers, wherein the set of pre-pre-amplifiers comprises a plurality of pairs of pre-pre-amplifiers, wherein the set of pre-pre-amplifiers comprises a pair of pre-pre-amplifiers specific for each of the pairs of target probes of the target probe set, wherein each pre-pre-amplifier of the pre-pre-amplifier pairs comprises a binding site for one of the target probes of the pair of target probes of a target probe set, and wherein the pre-pre-amplifiers comprise a plurality of binding sites for a pre-amplifier; (B) a set of pre-amplifiers, wherein the set of pre-amplifiers comprises a plurality of pre-amplifiers, wherein the plurality of pre-amplifiers comprise a pre-amplifier specific for each pair of pre-pre-amplifiers, wherein each pre-amplifier comprises binding sites for one of the pairs of pre-pre-amplifiers of the set of pre-pre-amplifiers and a plurality of binding sites for an amplifier; (C) a set of amplifiers, wherein the set of amplifiers comprises a plurality of subsets of amplifiers specific for each pre-amplifier specific for each pair of pre-pre-amplifiers, wherein the amplifiers of a subset of amplifiers comprise a binding site for one of the pre-amplifiers specific for a pair of pre-pre-amplifiers and a plurality of binding sites for a label probe; (D) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes can specifically label a first subset of target nucleic acids; (E) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes can specifically label a second subset of target nucleic acids that is different than the first subset of target nucleic acids; and.

In one embodiment, the kit further comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes can specifically label a third subset of target nucleic acids that is different than the first and second subsets of target nucleic acids.

In one embodiment, the kit comprises one or more target probe sets, wherein each target probe set comprises a pair of target probes that specifically hybridize to a target nucleic acid. In one embodiment, each target probe set comprises two or more pairs of target probes that can specifically hybridize to the same target nucleic acid.

In one embodiment, the kit comprises at least one reagent for permeabilizing cells.

The invention also provides a method of detecting a plurality of target nucleic acids comprising (A) contacting a sample comprising a cell comprising a plurality of nucleic acids with a plurality of target probe sets, wherein each target probe set comprises a pair of target probes that specifically hybridize to a target nucleic acid; (B) contacting the sample with a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier; (C) contacting the sample with a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier; (D) contacting the sample with a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe; (E) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes specifically label a first subset of target nucleic acids hybridized to the plurality of target probe sets; (F) detecting the label probes of the first set of label probes bound to the target nucleic acids, thereby detecting the first subset of target nucleic acids; (G) incubating the sample at a temperature above the melting temperature between the label probes and amplifiers and lower than the melting temperature between the target probes, pre-pre-amplifiers, pre-amplifiers and amplifiers, thereby removing the labels from the first set of label probes bound to the first subset of target nucleic acids; (H) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes specifically label a second subset of target nucleic acids hybridized to the plurality of target probe sets that is different than the first subset of target nucleic acids; and (I) detecting the label probes of the second set of label probes bound to the target nucleic acids, thereby detecting the second subset of target nucleic acids; wherein a plurality of target nucleic acids are detected.

In one embodiment, the method further comprises (J) incubating the sample at a temperature above the melting temperature between the label probes and amplifiers and lower than the melting temperature between the target probes, pre-pre-amplifiers, pre-amplifiers and amplifiers, thereby removing the labels from the second set of label probes bound to the second set of target nucleic acids; (K) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes specifically label a third subset of target nucleic acids hybridized to the plurality of target probe sets that is different than the first and second subsets of target nucleic acids; and (L) detecting the label probes of the third set of label probes bound to the target nucleic acids, thereby detecting the third subset of target nucleic acids.

In one embodiment, the method comprises repeating steps (J) through (L) one or more times.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample. In one embodiment, the sample is a cytological sample or is derived from a cytological sample.

In one embodiment, the invention additionally provides a sample of fixed and/or permeabilized cells, comprising (A) at least one fixed and/or permeabilized cell containing a plurality of target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier, wherein the pre-pre-amplifiers are hybridized to the respective specific target probe pairs; (D) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier, wherein the pre-amplifiers are hybridized to the respective pre-pre-amplifiers specific for the target probe sets; (E) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the sample comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the sample comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample. In one embodiment, the sample is a cytological sample or is derived from a cytological sample.

In one embodiment, invention additionally provides a slide comprising (A) a slide having immobilized thereon a plurality of fixed and/or permeabilized cells comprising at least one fixed and/or permeabilized cell containing target nucleic acids; (B) a plurality of target probe sets, wherein each target probe set comprises a pair of target probes specifically hybridized to target nucleic acids; (C) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier, wherein the pre-pre-amplifiers are hybridized to the respective specific target probe pairs; (D) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier, wherein the pre-amplifiers are hybridized to the respective pre-pre-amplifiers specific for the target probe sets; (E) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe, wherein the amplifiers are hybridized to the respective pre-amplifiers; (F) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes are hybridized to the respective amplifiers and specifically label a first subset of target nucleic acids hybridized to the plurality of target probe sets; wherein the hybridizations provide a detectable label on the first subset of target nucleic acids.

In one embodiment, the labels of the first set of label probes bound to the first subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the slide comprises a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes are hybridized to the respective amplifiers and specifically label a second subset of target nucleic acids hybridized to the plurality of target probe sets that is different than the first subset of target nucleic acids, wherein the hybridizations provide a detectable label on the second subset of target nucleic acids.

In one embodiment, the labels from the second set of label probes bound to the second subset of target nucleic acids are removed by incubating the sample at a temperature above the melting temperature between the label probes and amplifiers and lower than the melting temperature between the target probes, pre-pre-amplifiers, pre-amplifiers and amplifiers.

In one embodiment, the slide comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes are hybridized to the respective amplifiers and specifically label a third subset of target nucleic acids hybridized to the plurality of target probe sets that is different than the first and second subsets of target nucleic acids, wherein the hybridizations provide a detectable label on the third subset of target nucleic acids.

In one embodiment, each target probe set comprises two or more pairs of target probes that specifically hybridize to the same target nucleic acid.

In one embodiment, the target nucleic acids are independently DNA or RNA. In one embodiment, the target nucleic acids that are RNA are independently selected from the group consisting of messenger RNA (mRNA), micro RNA (miRNA), ribosomal RNA (rRNA), mitochondrial RNA, and non-coding RNA.

In one embodiment, the sample is a tissue specimen or is derived from a tissue specimen. In one embodiment, the sample is a blood sample or is derived from a blood sample.

In one embodiment, the sample is a cytological sample or is derived from a cytological sample.

In one embodiment, the invention additionally provides a kit for in situ detection of target nucleic acids, comprising (A) a set of pre-pre-amplifiers, wherein the set of pre-pre-amplifiers comprises a plurality of pre-pre-amplifiers, wherein the plurality of pre-pre-amplifiers comprises a pre-pre-amplifier specific for each target probe set, wherein each pre-pre-amplifier comprises binding sites for the pair of target probes of one of the target probe sets and a plurality of binding sites for a pre-amplifier; (B) a set of pre-amplifiers, wherein the set of pre-amplifiers comprises a plurality of subsets of pre-amplifiers specific for each pre-pre-amplifier, wherein each subset of pre-amplifiers comprises a plurality of pre-amplifiers, wherein the pre-amplifiers of a subset of pre-amplifiers comprise a binding site for one of the pre-pre-amplifiers specific for a target probe set and a plurality of binding sites for an amplifier; (C) a set of amplifiers, wherein the set of amplifiers comprises a plurality of subsets of amplifiers specific for each subset of pre-amplifiers, wherein each subset of amplifiers comprises a plurality of amplifiers, wherein the amplifiers of a subset of amplifiers comprise a binding site for the pre-amplifiers of one of the subsets of pre-amplifiers and a plurality of binding sites for a label probe; (D) a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the melting temperature between the label probes and the amplifiers is lower than the melting temperature between the target probes, pre-pre-amplifiers, pre-amplifiers and amplifiers, and wherein the first set of label probes can specifically label a first subset of target nucleic acids; (E) a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the melting temperature between the label probes and the amplifiers is lower than the melting temperature between the target probes, pre-pre-amplifiers, pre-amplifiers and amplifiers, and wherein the second set of label probes can specifically label a second subset of target nucleic acids that is different than the first subset of target nucleic acids.

In one embodiment, the kit further comprises a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the melting temperature between the label probes and the amplifiers is lower than the melting temperature between the target probes, pre-pre-amplifiers, pre-amplifiers and amplifiers, and wherein the third set of label probes can specifically label a third subset of target nucleic acids that is different than the first and second subsets of target nucleic acids.

In one embodiment, the kit comprises one or more target probe sets, wherein each target probe set comprises a pair of target probes that specifically hybridize to a target nucleic acid. In one embodiment, each target probe set comprises two or more pairs of target probes that can specifically hybridize to the same target nucleic acid.

In one embodiment, the kit comprises at least one reagent for permeabilizing cells.

BRIEF DESCRIPTION OF THE DRAWINGS

FIG. 3A shows the binding of target probe pair 1 (TP1a and TP1b) to target nucleic acid 1. Pre-amplifier (PA1) is shown bound to the target probe pair (TP1a and TP1b). A plurality of amplifiers (AMP1) is shown bound to PA1. A plurality of label probes (LP1) is shown bound to the amplifiers. FIG. 3A shows a similar configuration for targets 2 and 3, with the components of the SGC (target probes, pre-amplifiers, amplifiers, label probes) specific for each of the respective targets. FIG. 3B shows a modification of the configuration shown in FIG. 3A. Shown in FIG. 3B is the labeling of two exemplary target nucleic acids with respective signal generating complexes (SGCs). FIG. 3B shows the binding of target probe pair 1 (TP1a and TP1b) to target nucleic acid 1. Pre-pre-amplifier (PPA1) is shown bound to the target probe pair (TP1a and TP1b). A plurality of pre-amplifiers (PA1) is shown bound to PPA1. A plurality of amplifiers (AMP1) is shown bound to PA1. The amplifiers are shown bound to one pre-amplifier for simplicity, but it is understood that the amplifiers can be bound to all of the pre-amplifiers. A plurality of label probes (LP1) is shown bound to the amplifiers. FIG. 3B shows a similar configuration for target 2, with the components of the SGC (target probes, pre-pre-amplifiers, pre-amplifiers, amplifiers, label probes) specific for each of the respective targets. Shown in FIG. 3C is orthogonal labeling of target nucleic acids based on a Basescope™ assay. Shown in FIG. 3C is the labeling of two exemplary target nucleic acids with respective signal generating complexes (SGCs). FIG. 3C shows the binding of target probe pair 1 (TP1a and TP1b) to target nucleic acid 1. A pair of pre-pre-amplifiers (PPA1a and PPA1b) are shown bound to respective target probe pairs (TP1a and TP1b). Pre-amplifier (PA1) is shown bound to the pre-pre-amplifier pairs (PPA1a and PPA1b). A plurality of amplifiers (AMP1) is shown bound to PA1. The amplifiers are shown bound to one pre-amplifier for simplicity, but it is understood that the amplifiers can be bound to all of the pre-amplifiers. A plurality of label probes (LP1) is shown bound to the amplifiers. FIG. 3C shows a similar configuration for target 2, with the components of the SGC (target probes, pre-pre-amplifiers, pre-amplifiers, amplifiers, label probes) specific for each of the respective targets.

FIG. 4A shows detection of the first round of visualization of labels bound to the target nucleic acids, RNA polymerase II subunit A (POLR2A), peptidyl-prolyl isomerase B (PPIB), ubiquitin C (UBC) and hypoxanthine phosphoribosyltransferase 1 (HPRT1) genes. POLR2A, PPIB, UBC and HPRT1 were labeled with the fluorophores Alexa 488, ATTO 550, ATTO 647N, and Alexa 750, respectively. On a separate slide, a negative control probe for the bacterial dihydrodipicolinate reductase (dapB) gene, using the same fluorescent labels, was used to assess non-specific background. Nuclei were stained with DAPI (4',6-diamidino-2-phenylindole) (blue). FIG. 4B shows detection of the second round of visualization of labels bound to the target nucleic acids, tubulin beta class I (TUBB), ribosomal protein L28 (RPL28), ribosomal protein L5 (RPL5) and beta-2 microglobulin (B2M) using the fluorophores Alexa 488, ATTO 550, ATTO 647N, and Alexa 750, respectively, following cleavage of the labels bound in the first round. FIG. 4C shows detection of the third round of visualization of labels bound to the target nucleic acids, actin beta (ACTB), lactate dehydrogenase A (LDHA), ribosomal protein lateral stalk subunit P0 (RPLP0) and glyceraldehyde-3-phosphate dehydrogenase (GAPDH) using the fluorophores Alexa 488, ATTO 550, ATTO 647N, and Alexa 750, respectively, following cleavage of the labels bound in the second round.

DETAILED DESCRIPTION OF THE INVENTION

Figure 1:
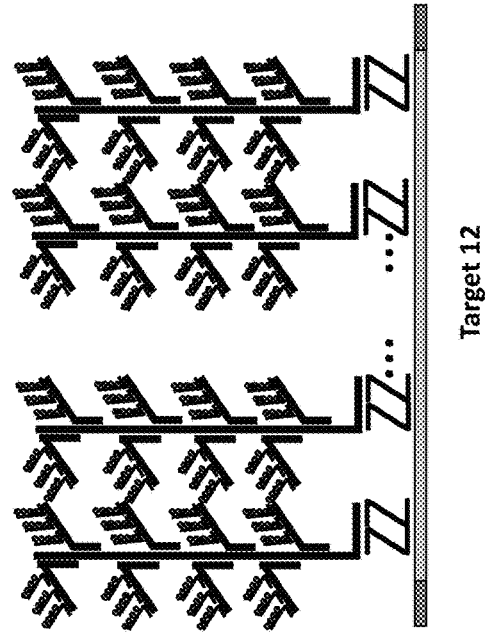
FIG. 1 shows a schematic diagram of a multiplexing assay. Certain embodiments of such an assay are referred to herein as an RNAscope™ HiPlex Probe Hybridization and Amplification System. In the embodiment depicted, the original RNAscope™ probe designs and branched-DNA-like signal amplification method (see, for example, U.S. Pat. No. 7,709,198, U.S. publications 2008/0038725 and 2009/0081688, WO 2007/001986, WO 2007/002006, Wang et al., *Expert Rev. Mol. Diagn.* 2(2):109-119 (2002)) was adopted to RNAscope™ HiPlex for multiplex detection of target nucleic acids. In the embodiment depicted in FIG. 1, twelve target sequences are simultaneously hybridized with probe pairs (depicted as double Z probes) that bind to 12 orthogonal signal amplification systems (indicated by the different colored label probes).
Figure 1:
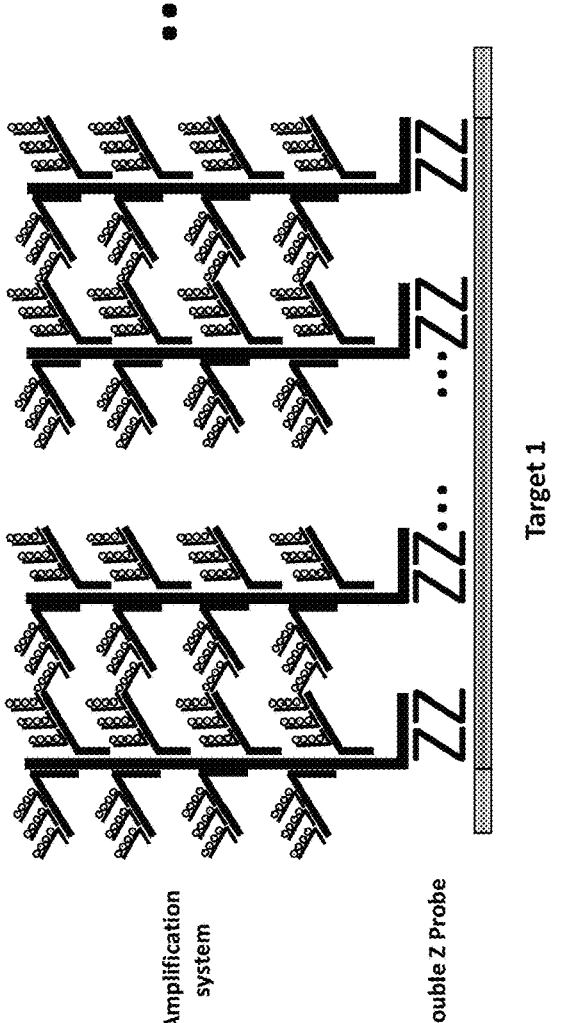

The present invention relates to methods for multiplex analysis of nucleic acids, for example, by in situ hybridization. The methods of the invention allow the detection of multiple target nucleic acids within the same sample and within the same cell.

One method of nucleic acid detection utilizes an RNA ISH technology called RNAscope™, which uses specially designed oligonucleotide probes, sometimes referred to as "double-Z" or ZZ probes, in combination with a branched-DNA-like signal amplification system to reliably detect RNA as small as 1 kilobase at single-molecule sensitivity under standard bright-field microscopy (Anderson et al., *J. Cell. Biochem.* 117(10):2201-2208 (2016); Wang et al., *J. Mol. Diagn.* 14(1):22-29 (2012)). Such a probe design greatly improves the specificity of signal amplification because only when both probes in each pair bind to their intended target can signal amplification occur. The RNAscope™ technology can distinguish up to four or five RNA targets simultaneously using fluorescent detection. However, a method using RNAscope™ for detecting greater than four to five targets has not previously been described.

Described herein is an assay and detection strategy that provides specific detection of two or more target nucleic acid sequences in an iterative fashion at single cell resolution using a detection system such as the RNAscope™ signal amplification system and fluorescent dyes with common spectral profiles. This is achieved by simultaneous target hybridization and amplification of all target sequences, followed by iterative detection of generally three to five nucleic acid targets in successive rounds. To provide the ability to perform iterative detection steps, the label, such as a fluorescent dye, is cleavable, for example chemically cleavable, allowing for subsequent rounds of detection using the same labels as in the first round. Within a round, fluorescent dye conjugates that can be spectrally separated using conventional fluorescent microscopy are utilized. The fluorescent dyes are then cleaved off. One exemplary cleaving agent is the reducing agent tris (2-carboxyethyl) phosphine (TCEP). Following cleavage of the detectable label, such as a fluorescent dye, subsequent rounds of target detection and imaging are carried out. The assay strategy eliminates the need to use harsh conditions to strip off the label probes from the previous round, which may disrupt the existing signal amplification complexes associated with the remaining targets, and also preserves tissue and RNA integrity for maximized detection.

The present invention relates to methods that allow for highly sensitive and specific detection of nucleic acid sequences in a cell. The methods of the invention have numerous practical applications in research and diagnostics (Hu et al., *Biomark. Res.* 2(1):1-13, doi: 10.1186/2050-7771-2-3 (2014); Ratan et al., *Cureus* 9(6):e1325. doi: 10.7759/cureus.1325 (2017); Weier et al., *Expert Rev. Mol. Diagn.* 2(2):109-119 (2002)). The methods of the invention can be used, for example, for mapping of spatial organization in highly complexed tissues such as the nervous system and tumor microenvironment, identifying known cell types and new cell types, identifying cellular states, detection of altered gene expression in diseased cells and tissues, localizing altered gene expression in specific cell types, analyzing tumor heterogeneity, detecting biomarkers for cancer diagnosis and prognosis or for other disease conditions, detecting biomarkers for companion diagnostics, and detection and identification of pathogens (for example, bacteria, viruses, fungi, microbial parasites.)

Figure 3A:
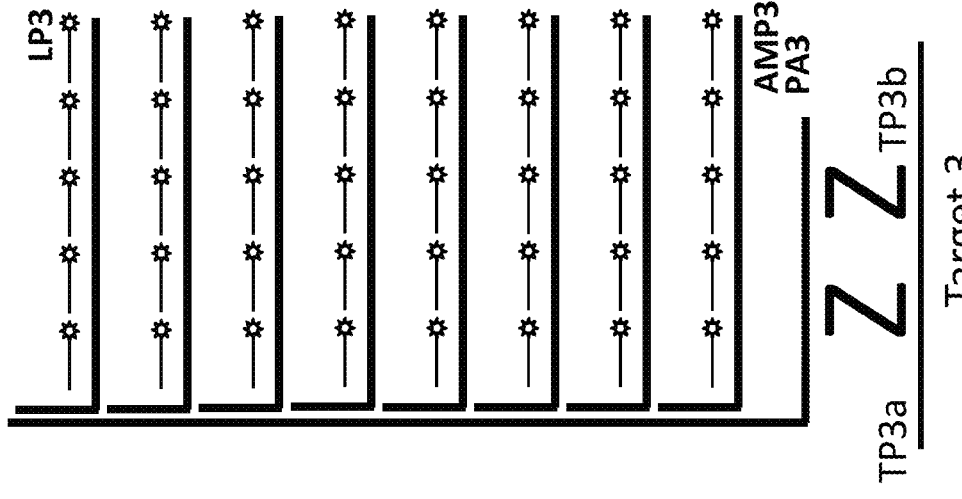
FIGS. 3A-3C show a schematic of orthogonal labeling of target nucleic acids. Shown in FIG. 3A is orthogonal labeling of target nucleic acids based on an RNAscope™ assay. Shown in FIG. 3A is the labeling of three exemplary target nucleic acids with respective signal generating complexes (SGCs).
Figure 3A:
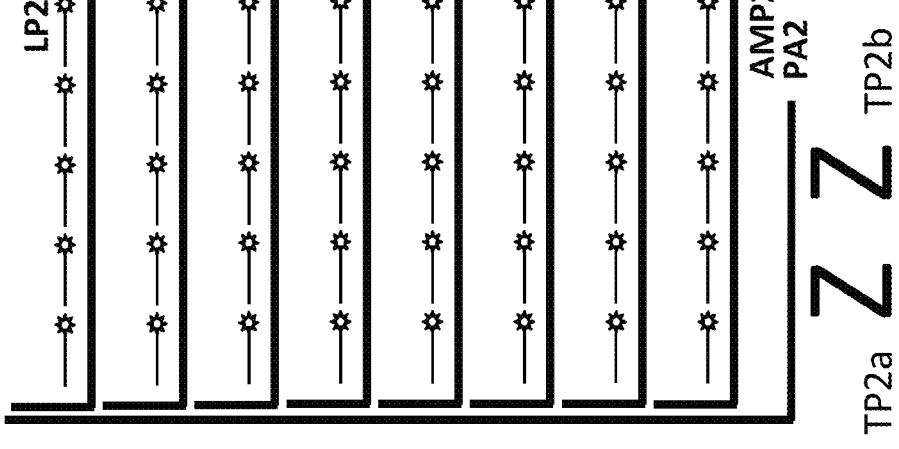
Figure 3A:
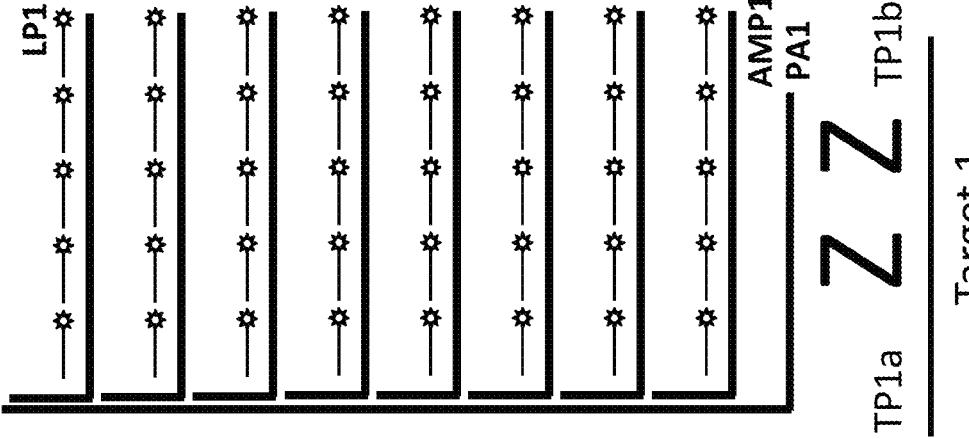
Figure 3B:
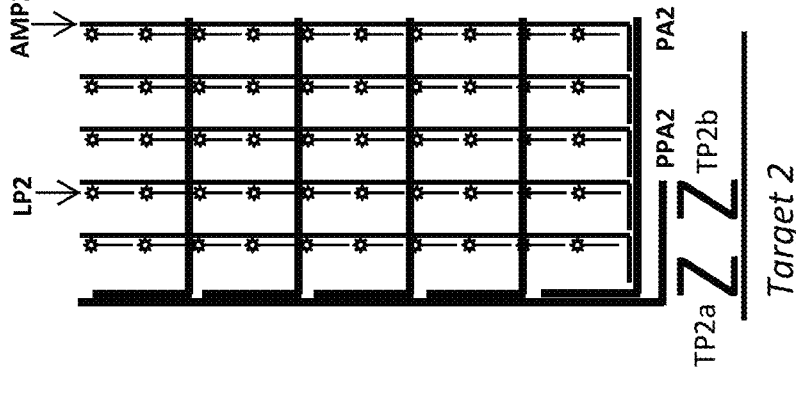
Figure 3B:
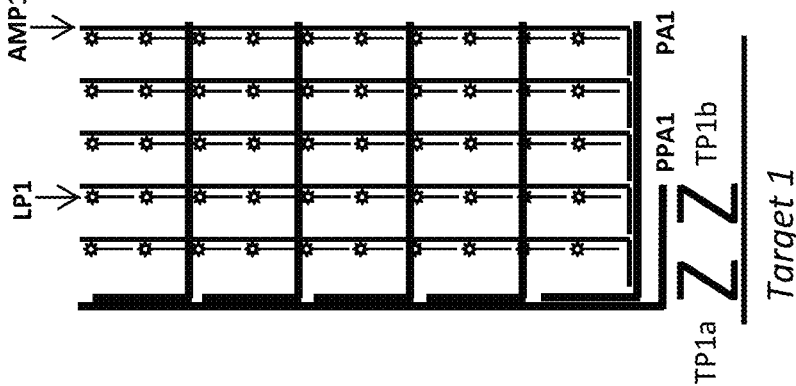

The present invention extends the probe design principle and the branched-DNA-like signal amplification at the core of the RNAscope™ technology (Wang et al., supra, 2012) to highly sensitive and specific sequence detection of multiple nucleic acid targets (greater than one target nucleic acid detected in an iterative fashion) in the same cell and/or tissue sections. Like RNAscope™ probes, each target probe contains a target binding segment (target binding site) that binds to a specific sequence in the target nucleic acid. The probes also contain a "tail" sequence that binds to signal amplification molecules, as described herein. Two probes bind as a pair to adjacent sites in the target nucleic acid sequence. Only when both probes bind to their respective target sites can a full binding site for the signal amplification molecules (for example, a pre-amplifier as in FIG. 3A or a pre-pre-amplifier as in FIGS. 3B and 3C) be formed, leading to successful signal amplification and detection. Probes for different target sequences are designed to have independent and distinct binding sequences for corresponding orthogonal amplification molecules. Such sequences can be readily designed using appropriate algorithms to achieve probe hybridization and signal amplification of multiple targets in parallel (see FIGS. 1 and 3). Targets are detected in multiple rounds using detectable labels, such as fluorophores, that are spectrally distinct within each round.

The same iterative assay design strategy can be used with the Basescope™ signal amplification system (Baker et al., *Nat. Commun.* 8(1):1998, doi: 10.1038/s41467-017-02295-5 (2017)), which can be applied to detect short sequences. The methods can also be applied to DNA detection of multiple targets. The methods of the invention can also be applied to other signal amplification methods known in the art such as hybridization chain reaction (HCR) (Choi et al., *Development* 145(12), pii: dev165753, doi: 10.1242/dev.165753 (2018)). The latest version of HCR (HCR v3.0) employs a similar paired probe design as RNAscope™ (Choi et al., supra, 2018). Other signal amplification systems to which the methods of the invention can be applied include, but are not limited to, rolling circle amplification (Larsson et al., *Nature Methods* 7(5):395-397 (2010); clampFISH (Rouhanifard et al., *BioRxiv*, 222794 (doi.org/10.1101/222794)(2018); and SABER (Kishi et al., *Nat. Methods* 16:533-544 (2019)).

The methods of the invention can be used to label multiple gene targets in a single cell and/or tissue section with the same level of sensitivity and specificity of the RNAscope™ technology. It can be used with both fluorescence-based detection as well as imaging mass cytometry (Schulz et al., *Cell Syst.* 6(1):25-36 (2018)) for detecting high numbers of biomarkers in the spatial context of the tissue microenvironment. The methods can be used in research and diagnostic applications.

In FIGS. 1-3 and 6, the target probes are depicted in a "Z" configuration, as described, for example, in U.S. Pat. No. 7,709,198, U.S. publications 2008/0038725 and 2009/0081688, and WO 2007/001986 and WO 2007/002006. The Z configuration shown in FIGS. 1-3 and 6 has the target binding site 5' to the pre-amplifier (FIGS. 3A and 6A) or pre-pre-amplifier (FIGS. 3B, 3C, 6B and 6C) binding site of the target probe. It is understood that such a configuration, as depicted in FIGS. 1-3 and 6, is merely exemplary, and the orientation can be the reverse, that is, the target binding site can be 3' to the pre-amplifier or pre-pre-amplifier binding site. It is understood that the target probe pair can independently be in either orientation, that is, one member of the pair of target probes can have the target binding site 5' or 3' to the pre-amplifier or pre-pre-amplifier binding site, and can be paired with a second probe having a binding site 5' or 3' to the pre-amplifier or pre-pre-amplifier.

As used herein, the term "label probe" refers to an entity that binds to a target molecule, directly or indirectly, generally indirectly, and allows the target to be detected. A label probe (or "LP") contains a nucleic acid binding portion that is typically a single stranded polynucleotide or oligonucleotide that comprises one or more labels which directly or indirectly provides a detectable signal. The label can be covalently attached to the polynucleotide, or the polynucleotide can be configured to bind to the label. For example, a biotinylated polynucleotide can bind a streptavidin-associated label. The label probe can, for example, hybridize directly to a target nucleic acid. In general, the label probe can hybridize to a nucleic acid that is in turn hybridized to the target nucleic acid or to one or more other nucleic acids that are hybridized to the target nucleic acid. Thus, the label probe can comprise a polynucleotide sequence that is complementary to a polynucleotide sequence, particularly a portion, of the target nucleic acid. Alternatively, the label probe can comprise at least one polynucleotide sequence that is complementary to a polynucleotide sequence in an amplifier, pre-amplifier, pre-pre-amplifier, signal generating complex (SGC), or the like, as described herein. In general in embodiments of the invention, the label probe binds to an amplifier. As used herein, a label probe comprising an enzyme label refers to a label probe comprising a nucleic acid binding portion such as an oligonucleotide and an enzyme that is coupled to the nucleic acid binding portion. As disclosed herein, the coupling of the enzyme to the nucleic acid binding portion can be covalent or through a high affinity binding interaction such as biotin/avidin or other similar high affinity binding molecules.

As used herein, a "target probe" is a polynucleotide that is capable of hybridizing to a target nucleic acid and capturing or binding a label probe or signal generating complex (SGC) component, for example, an amplifier, pre-amplifier or pre-pre-amplifier, to that target nucleic acid. The target probe can hybridize directly to the label probe, or it can hybridize to one or more nucleic acids that in turn hybridize to the label probe; for example, the target probe can hybridize to an amplifier, a pre-amplifier or a pre-pre-amplifier in an SGC. The target probe thus includes a first polynucleotide sequence that is complementary to a polynucleotide sequence of the target nucleic acid and a second polynucleotide sequence that is complementary to a polynucleotide sequence of the label probe, amplifier, pre-amplifier, pre-pre-amplifier, or the like. In general in embodiments of the invention, the target probe binds to a pre-amplifier, as in FIGS. 3A and 6A, or to a pre-pre-amplifier, as in FIGS. 3B, 3C, 6B and 6C. The target probe is generally single stranded so that the complementary sequence is available to hybridize with a corresponding target nucleic acid, label probe, amplifier, pre-amplifier or pre-pre-amplifier. In embodiments of the invention, the target probes are provided as a pair.

As used herein, an "amplifier" is a molecule, typically a polynucleotide, that is capable of hybridizing to multiple label probes. Typically, the amplifier hybridizes to multiple identical label probes. The amplifier can also hybridize to a target nucleic acid, to at least one target probe of a pair of target probes, to both target probes of a pair of target probes, or to nucleic acid bound to a target probe such as an amplifier, pre-amplifier or pre-pre-amplifier. For example, the amplifier can hybridize to at least one target probe and to a plurality of label probes, or to a pre-amplifier and a plurality of label probes. In general in embodiments of the invention, the amplifier can hybridize to a pre-amplifier. The amplifier can be, for example, a linear, forked, comb-like, or branched nucleic acid. As described herein for all polynucleotides, the amplifier can include modified nucleotides and/or nonstandard internucleotide linkages as well as standard deoxyribonucleotides, ribonucleotides, and/or phosphodiester bonds. Suitable amplifiers are described, for example, in U.S. Pat. Nos. 5,635,352, 5,124,246, 5,710,264, 5,849,481, and 7,709,198 and U.S. publications 2008/0038725 and 2009/0081688, each of which is incorporated by reference. In general in embodiments of the invention, the amplifier binds to a pre-amplifier and label probes (see FIGS. 3 and 6).

As used herein, a "pre-amplifier" is a molecule, typically a polynucleotide, that serves as an intermediate binding component between one or more target probes and one or more amplifiers. Typically, the pre-amplifier hybridizes simultaneously to one or more target probes and to a plurality of amplifiers. Exemplary pre-amplifiers are described, for example, in U.S. Pat. Nos. 5,635,352, 5,681, 697 and 7,709,198 and U.S. publications 2008/0038725, 2009/0081688 and 2017/0101672, each of which is incorporated by reference. In general in embodiments of the invention, a pre-amplifier binds to both members of a target probe pair (see FIGS. 3A and 6A), to a pre-pre-amplifier that can bind to a target probe pair (FIGS. 3B and 6B), or to both members of a pair of pre-pre-amplifiers that can bind to a target probe pair (see FIGS. 3C and 6C). A pre-amplifier also binds to an amplifier (see FIGS. 3 and 6).

As used herein, a "pre-pre-amplifier" is a molecule, typically a polynucleotide, that serves as an intermediate binding component between one or more target probes and one or more pre-amplifiers. Typically, the pre-pre-amplifier hybridizes simultaneously to one or more target probes and to a plurality of pre-amplifiers. Exemplary pre-pre-amplifiers are described, for example, in 2017/0101672, which is incorporated by reference. In general in embodiments of the invention, a pre-pre-amplifier binds to a target probe pair (see FIGS. 3B and 6B) or to a member of a target probe pair (see FIGS. 3C and 6C) and to a pre-amplifier.

As used herein, the term "plurality" is understood to mean two or more. Thus, a plurality can refer to, for example, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 300 or more, 400 or more, 500 or more, 600 or more, 700 or more, 800 or more, 900 or more, or 1000 or more, or even a greater number, if desired for a particular use.

As described herein, the invention relates to multiplex detection of target nucleic acids, where the methods provide for detection of higher numbers of target nucleic acids than previously described methods of in situ hybridization. An exemplary embodiment is depicted in FIG. 1, in which the detection of twelve target nucleic acids is depicted. In particular, the methods can employ orthogonal amplification systems to distinctly detect multiple target nucleic acids in iterative rounds of detection.

Figure 2:
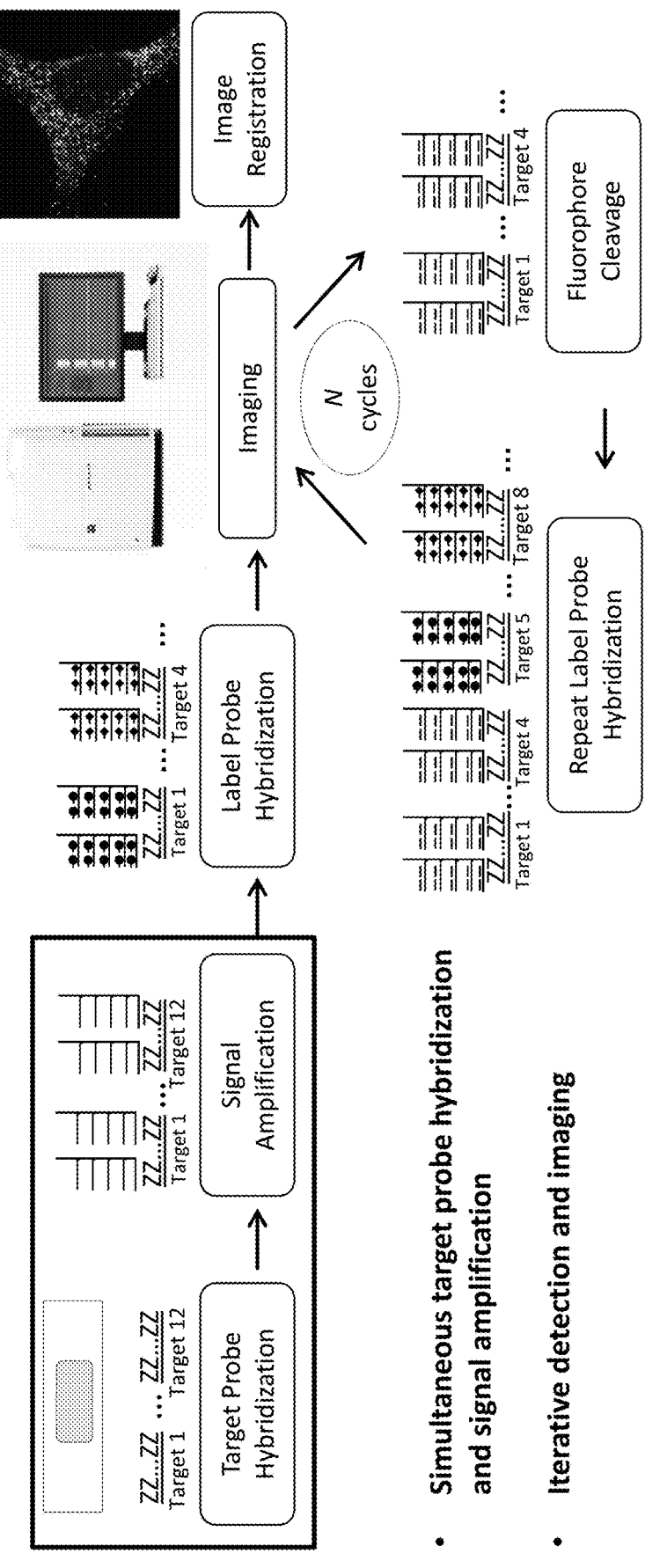
FIG. 2 shows a schematic of workflow of a multiplex assay (RNAscope™ HiPlex Assay Workflow). In the embodiment depicted in FIG. 2, twelve target sequences are hybridized to target probes (depicted as double Z probes), and signals are amplified through an amplification system, such as RNAscope™, simultaneously. In the embodiment depicted, the first four targets are detected via four non-spectral overlapping fluorescent dye-conjugated oligos (Label Probes) and imaged using a conventional fluorescent microscope or scanner. Fluorophores are then cleaved off of the label probes and the next four targets are labeled and imaged using the same method. After L (e.g., three) rounds of detection of four targets each, images are registered using an image registration software algorithm to create the final composite of superimposed images with single-cell resolution.

As shown in FIG. 2, in one embodiment the methods of the invention employ simultaneous hybridization of target probes for multiple target nucleic acids and an amplification system for detection of the target nucleic acids. However, rather than detecting all of the target nucleic acids at once, the labeling and detection of the target nucleic acids are done in iterative rounds, where only a subset of the target nucleic acids to which target probes bind are detected in the first round. This is depicted schematically in FIG. 2 as detection of Targets 1-4 in the first round. Following imaging of the detectable labels bound to target nucleic acids (Targets 1-4 in FIG. 2) in the first round, the labels are removed from the sample by employing a cleavable label ("fluorophore cleavage" in FIG. 2). Once the labels bound to target nucleic acids in the first round have been cleaved, a second round of detection is applied by adding a second group of labels that detect, generally, a different subset of target nucleic acids (depicted as Targets 5-8 in FIG. 2). By cleaving the first round of labels from the target nucleic acids, the same detectable labels (depicted as fluorophores in FIG. 2) can be used in the second round as in the first round. Such a cycle of cleaving labels bound to the target nucleic acids and adding labels to detect a new subset of target nucleic acids allows the detection of many more nucleic acid targets in the same sample and the same cells than previously described methods.

The methods of the invention utilize L (L=1, 2, 3, . . . ) rounds (labeled "N cycles" in FIG. 2) of iterative fluorescent labeling of I (I=2, 3, 4, . . . ) targets followed by imaging and cleavage of the label, illustrated in FIG. 2 as fluorophore cleavage. The iterative detection method provides for simultaneous visualization of L×I distinct target sequences (N) from a single round of hybridization and amplification step. The "N" indicates the total number of targets to be detected, and "I" described above indicates the number of targets per iteration, in each of the L rounds. Generally, the number of targets (I) in each iterative round of labeling will be 2 or more, 3 or more, 4 or more, and so forth up to the number that can be distinctly labeled and detected in a single round, as disclosed herein. If desired, a single target nucleic acid (I=1) can be detected in a round. In some embodiments, the number of targets in I can be different in each round. For example, in three rounds of detection, where I is 4, 4 and 1 in each respective round, a total of 9 targets would be detected. Thus, the number of targets N=sum (i1, i2, i3 . . . iL), where i1, i2, i3 are the number of targets detected in each iterative round, which can be identical or different, and L is the total number of rounds. In the case where the number "i" is identical in each round, N=L×I.

In general, when using distinct and distinguishable labels for multiplex detection of target nucleic acids, there is a limit to the number of distinct labels that can be distinguished concurrently. For example, in the case of fluorescent labels, in order for multiple labels to be detected simultaneously, there should be spectral separation of the multiple emissions from the fluorophores so that the fluorescence microscope can distinguish the fluorophores concurrently. The need for spectral separation of the emissions from the fluorophores limits the number of fluorophores that can be visualized simultaneously. The present invention circumvents this limitation by detecting labels iteratively, such that the same fluorophores can be used in sequential rounds to detect different target nucleic acids.

The orthogonal nature of the detection systems that can be used in the methods of the invention is depicted in FIG. 3. FIG. 3A shows one embodiment of the invention, with three exemplary target nucleic acids and the respective orthogonal detection systems, also referred to herein as signal generating complexes (SGCs). As depicted in FIG. 3A, each of the target nucleic acids is hybridized to specific target probe pairs (TP1a and TP1b, TP2a and TP2b, TP3a and TP3b), which in turn are hybridized to respective specific preamplifiers (PA1, PA2, PA3), which in turn are hybridized to a respective specific plurality of amplifiers (AMP1, AMP2, AMP3), which are in turn hybridized to a respective specific plurality of label probes (LP1, LP2, LP3). FIG. 3B shows another embodiment of the invention, with two exemplary target nucleic acids and the respective orthogonal detection systems. As depicted in FIG. 3B, each of the target nucleic acids is hybridized to specific target probe pairs (TP1a and TP1b, TP2a and TP2b), which in turn are hybridized to respective specific pre-pre-amplifiers (PPA1, PPA2), which in turn are hybridized to respective specific plurality of pre-amplifiers (PA1, PA2), which in turn are hybridized to a respective specific plurality of amplifiers (AMP1, AMP2), which are in turn hybridized to a respective specific plurality of label probes (LP1, LP2). FIG. 3C shows another embodiment of the invention, with two exemplary target nucleic acids and the respective orthogonal detection systems. As depicted in FIG. 3C, each of the target nucleic acids is hybridized to specific target probe pairs (TP1a and TP1b, TP2a and TP2b), which in turn are hybridized to respective specific pairs of pre-pre-amplifiers (PPA1a and PPA1b, PPA2a and PPA2b), which in turn are both hybridized to respective specific pre-amplifiers (PA1 and PA2), which in turn are hybridized to respective specific amplifiers (AMP1 and AMP2), which in turn are hybridized to respective specific label probes (LP1 and LP2). For simplicity, a plurality of amplifiers are depicted bound to one of the pre-amplifiers, but it is understood that the amplifiers can bind to each of the pre-amplifiers. As shown in FIG. 3, each nucleic acid target has a specific detection system, for which binding of the components are mediated by unique binding sites that provide for binding to one specific complex but not to another. Such unique binding sites for hybridization of components of an SGC to a specific target nucleic acid can be achieved designing binding sites (nucleic acid sequences) to provide the desired specificity, as well known in the art and described herein. This orthogonal detection system, where each target is uniquely labeled, allows the detection of multiple target nucleic acids in the same sample.

Thus, the invention relates to the use of unique labeling of multiple nucleic acid targets and the iterative detection of subsets of the target nucleic acids to achieve a higher multiplex detection of target nucleic acids. The effectiveness of the methods of the invention for multiplex detection of target nucleic acids in iterative rounds has been demonstrated herein, as described in the Examples.

In some embodiments, a single target nucleic acid is detected in each round. In such a case, rather than contacting a sample with a plurality of target probe sets directed to multiple target nucleic acids, the sample is contacted with a target probe set that can specifically hybridize to a target nucleic acid.

The invention is based on utilizing orthogonal amplification systems to uniquely label target nucleic acids so that multiple target nucleic acids can be analyzed in the same sample and even in the same cell. The invention utilizes the building of signal generating complexes (SGCs) that are specific for particular target nucleic acids so that each target nucleic acid can be uniquely identified. In one embodiment, a sample is contacted with target probe sets comprising a pair of target probes that can specifically hybridize to a target nucleic acid. The sample is also contacted with a set of pre-amplifiers that includes a pre-amplifier specific for each target probe set and that can hybridize to the target probe pair that is hybridized to the respective target nucleic acid. Such an embodiment is illustrated schematically in FIG. 3A. The sample is also contacted with amplifiers, where the amplifiers include subsets of amplifiers specific for each pre-amplifier that is specific for a target probe pair that is specific for a target nucleic acid. Thus, each target nucleic acid has an assembly of unique components of an SGC, target probe pair(s), pre-amplifiers, and amplifiers, that provide discrimination between the target nucleic acids. In an additional embodiment, a pre-pre-amplifier can bind to a target probe pair as an additional amplification layer between the target probe pairs and the pre-amplifier (see FIGS. 3B and 6B).

In another embodiment, a sample is contacted with target probe sets comprising a pair of target probes that can specifically hybridize to a target nucleic acid. The sample is also contacted with a set of pre-pre-amplifiers that includes a pair of pre-pre-amplifiers specific for each target probe set and that can hybridize to the target probe pair that is hybridized to the respective target nucleic acid. Such an embodiment is illustrated schematically in FIG. 3C. The sample is also contacted with a set of pre-amplifiers that includes a pre-amplifier that can specifically bind to both pairs of pre-pre-amplifiers that are specific for a pair of target probes that are specific for a target nucleic acid. The sample is also contacted with amplifiers, where the amplifiers include subsets of amplifiers specific for each pre-amplifier that is specific for a pair of pre-pre-amplifiers that are specific for a target probe pair that is specific for a target nucleic acid. Thus, each target nucleic acid has an assembly of unique components of an SGC, target probe pairs, pre-pre-amplifiers, pre-amplifiers, and amplifiers, that provide discrimination between the target nucleic acids.

In order to detect the target nucleic acids, sets of label probes are contacted with the sample. Instead of contacting the sample with label probes that can detect all of the target nucleic acids, the sample is contacted with a set of label probes that can detect a subset of the target nucleic acids. Thus, rather than detecting all of the target nucleic acids at once, the target nucleic acids are detected in iterative rounds of detection. Within one round, the label probes specific for the respective target nucleic acids are distinguishable from each other, so that all of the target nucleic acids associated with a first round of applied label probes can be detected concurrently.

The number of target nucleic acids that can be detected concurrently in a single round will depend on the type of label used in the label probes and how such labels can be distinguished. For example, in the case of using fluorescent labels, the fluorophores used in a single round need to be distinguishable, so there should be spectral separation of the emissions of the fluorophores. The number of fluorophores that can be distinguished concurrently is up to 10, depending on the detection system and the availability of filters and/or software that can be used to distinguish fluorophores with overlapping emissions, which are considered to have spectral separation if they can be distinguished, as is well known in the art. Imaging systems for detecting multiple fluorescent labels are well known in the art (for example, Vectra Polaris, Perkin Elmer, Waltham MA).

In one embodiment, the methods of the invention are applied to the detection of one or more target nucleic acids per round, for example, 1, 2, 3, 4, 5, 6, 7, 8, 9, 10, or more target nucleic acids are detected in each round. As disclosed herein, a person skilled in the art can select suitable distinct labels and a suitable number of rounds of detection to allow detection of a desired number of target nucleic acids in a sample.

In order to take advantage of the distinguishable characteristics of the labels used in the first round of detection in subsequent rounds, in some embodiments the labels on the label probes are cleavable. Thus, once a first round of detection of a subset of the target nucleic acids has been carried out, the labels attached to the target nucleic acids are cleaved to remove the labels from the first subset of target nucleic acids. Exemplary cleavable conjugates of labels to the label probes are described herein. Once the labels are cleaved, a second round of detection is carried out by contacting the sample with a second set of label probes that are specific, generally, for different target nucleic acids than detected in the first round. Since the labels of the first round have been cleaved from the respective target nucleic acids, the same distinguishable labels can now be used in the label probes of the second round of detection. It is understood that, while the same labels can be used in iterative rounds of detection of subsets of target nucleic acids, it is not required that the same labels be used in sequential rounds of detection, so long as the labels used in the same round are distinguishable.

Once a second round of detection of a subset of target nucleic acids has been carried out, optionally one or more additional rounds of cleavage, labeling and detection can be applied to the sample. For example, after detection of a second subset of target nucleic acids, the labels can be cleaved from the SGCs assembled on the second subset of target nucleic acids and a third round of labeling and detection can be carried out to detect a third subset of target nucleic acids that are distinct from the first and second subsets of target nucleic acids. Such iterative rounds of detection of target nucleic acids can be carried out to detect a desired number of multiple target nucleic acids using a desired number of iterations of detection. It is understood that, on the final iterative round of detection, it is not necessary for the label probe to comprise a cleavable label, since no further rounds of detection are to be performed. Thus, on the final iterative round of detection, it is optional to use a label probe that comprises a cleavable label, that is, the label probe can comprise a cleavable label, or not. Generally the rounds of detection are carried out such that different target nucleic acids are detected in each round. However, it is understood that subsequent rounds of detection can include, in some embodiments, detection of target nucleic acid(s) that overlap with previous rounds, so long as the subset of target nucleic acids detected in each sequential round are different from each other. In another embodiment, sequential rounds of detection can be performed on the same target nucleic acid, if desired. Thus, in some embodiments, the same target nucleic acids or overlapping target nucleic acids can be detected in one or more sequential rounds. Such a detection of the same target nucleic acids or overlapping target nucleic acids in sequential rounds can be used to generate a temporal barcode to each target nucleic acid when the same target nucleic acids are detected in each round in a pre-determined sequence of colors. Such methods have been described previously, for example, as Sequential bar-coded Fluorescence in situ Hybridization (seqFISH) (see Shah et al., *Neuron* 92(2):342-357 (2016)).

The methods of the invention are applied to multiplex detection of target nucleic acids. As disclosed herein, the methods of the invention are carried out in iterative rounds of detection of subsets of target nucleic acids. As also disclosed herein, the number of target nucleic acids that can be detected in one round depends on the type of label probe being used and the ability to distinguish the label probes specific for different target nucleic acids when concurrently detected. Higher levels of multiplexing are achieved by iterative rounds of detection. For example, in the exemplary embodiment depicted in FIG. 2, one round of labeling and detection provides detection of four target nucleic acids, a second round of labeling and detection provides detection of eight target nucleic acids, and a third round of labeling and detection provides detection of twelve target nucleic acids. A person skilled in the art can readily determine a desired number of target nucleic acids to detect in assays of the invention. In some embodiments, two rounds of labeling and detecting are used in methods of the invention. In some embodiments, three rounds of labeling and detecting are used. In some embodiments, 4, 5, 6, 7, 8, 9 or 10 rounds or greater of labeling and detecting can be used so long as there are a sufficient number of SGCs available to uniquely label and detect each target nucleic acid and the SGCs remain sufficiently bound to the target nucleic acids during the assay conditions to detect the target nucleic acids. A person skilled in the art can readily determine the number of rounds of labeling and detection that can be applied in methods of the invention, where the target nucleic acids can be detected in each round.

As subsequent rounds of detection are applied to the sample, the subsequently obtained detection of target nucleic acids can be registered with the previously detected round(s) of target nucleic acid detection so that the expression of all of the detected target nucleic acids can be determined in the same sample and even in the same cell (see FIG. 2). The registration of rounds of target nucleic acid detection can be achieved using image analysis software to superimpose the images of target nucleic acids detected in different rounds. Such registration algorithms for aligning and superimposing multiple images are well known in the art, for example, the Scale-Invariant Feature Transform (SIFT) algorithm (Lowe "Distinctive Image Features from Scale-Invariant Keypoints", *Internat. J. Computer Vision*

60(2): 91-110 (2004)). Essentially, these algorithms compare an input image with a reference image to generate a transformation matrix to account for shifting and rotation. Tools exist, for example, in ImageJ, that can automatically perform this task (imagej.net/Registration) (Schneider et al., *Nature Methods* 9(7):671-675 (2012); Schindelin et al., *Mol. Reprod. Dev.* 82(7-8):518-529 (2015)).

Additional multiplexing can be achieved by utilizing the same SGC assemblies but with different target probe sets directed to different target nucleic acids. In such a case, after detecting an initial set of target nucleic acids with SGC complexes detected in iterative rounds of labeling of subsets of target nucleic acids, the SGC complexes can be removed from the target nucleic acids using appropriate conditions to denature the hybridization of the SGC to the target nucleic acids. Once the SGC complexes have been removed from the sample, the same pre-amplifiers/amplifiers/label probes or pre-pre-amplifiers/pre-amplifiers/amplifiers/label probes can be used with target probe sets designed to be specific for a different set of target nucleic acids than detected in the first round of SGC detections. In this way, detection of additional target nucleic acids can be achieved.

In still another embodiment, the methods of the invention can be applied to simultaneous detection of double stranded nucleic acids and single stranded nucleic acids, for example, detection of DNA and RNA in the same sample. In such a case, probes can be designed to detect single stranded nucleic acids, such as RNA (see, for example, U.S. Pat. No. 7,709,198, U.S. publications 2008/0038725 and 2009/0081688, and 2017/0101672) and double stranded nucleic acids such that both double stranded nucleic acids and single stranded nucleic acids, such as DNA and RNA, can be detected in the same sample.

In some embodiments of the invention, each target probe set that is specific for a target nucleic acid comprises two or more pairs of target probes that specifically hybridize to the same target nucleic acid. In such a case, the pairs of target probes in the target probe set specific for a target nucleic acid bind to different and non-overlapping sequences of the target nucleic acid. When a target probe set is used that has two or more pairs of target probes that can specifically hybridize to the same target nucleic acid, the molecule that binds to the target probe pairs, either a pre-amplifier (see FIGS. 1, 3A and 6A), or a pre-pre-amplifier (see FIGS. 3B, 3C, 6B and 6C), generally are the same for target probe pairs in the same target probe set (see FIG. 1, which shows the same pre-pre-amplifier bound to the multiple target probe pairs for the same target). Thus, the target probe pairs that bind to the same target nucleic acid can be designed to comprise the same binding site for the molecule in the SGC that binds to the target probe pairs, that is, a pre-amplifier or pre-pre-amplifier. Such an embodiment is exemplified in FIG. 1, which schematically shows four target probe pairs bound to the respect target nucleic acids and depicts a number greater than four bound to the target nucleic acid (represented by " . . . "). The use of multiple target probe pairs to detect a target nucleic acid provides for a higher signal associated with the assembly of multiple SGCs on the same target nucleic acid. In some embodiments, the number of target probe pairs used for binding to the same target nucleic acid are in the range of 1-10, 1-20, 1-30, 1-40, 1-50, 1-60, 1-70, 1-80, 1-90, 1-100, 1-110, 1-120, 1-130, 1-140, 1-150, 1-160, 1-170, 1-180, 1-190, or 1-200 pairs per target, or larger numbers of pairs, or any integer number of pairs in between, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, and the like.

The methods of the invention can be utilized to achieve the detection of desired target nucleic acids. In one embodiment, a target nucleic acid is detected with a plurality of target probe pairs. In such a case, target probe pairs are designed to bind to more than one region of a target nucleic acid to allow for the assembly of multiple SGCs onto a target nucleic acid. It is understood that the target binding sites of one target probe pair do not overlap with the target binding sites of another target probe pair if a plurality of target probe pairs are being used to bind to the same target nucleic acid.

In an embodiment of the invention, the target nucleic acids detected by the methods of the invention can be any nucleic acid present in the cell sample, including but not limited to, RNA, including messenger RNA (mRNA), micro RNA (miRNA), ribosomal RNA (rRNA), mitochondrial RNA, non-coding RNA, and the like, or DNA, and the like. In a particular embodiment, the nucleic acid is RNA. In the methods of the invention for multiplex detection of nucleic acids, it is understood the target nucleic acids can independently be DNA or RNA. In other words, the target nucleic acids to be detected can be, but are not necessarily, the same type of nucleic acid. Thus, the target nucleic acids to be detected in an assay of the invention can be DNA and RNA. In the case where the target nucleic acids are RNA, it is understood that the target nucleic acids can independently be selected from the group consisting of messenger RNA (mRNA), micro RNA (miRNA), ribosomal RNA (rRNA), mitochondrial RNA, and non-coding RNA. Thus, the target nucleic acids can independently be DNA or any type of RNA.

As described herein, the methods of the invention generally relate to in situ detection of target nucleic acids. Methods for in situ detection of nucleic acids are well known to those skilled in the art (see, for example, US 2008/0038725; US 2009/0081688; Hicks et al., *J. Mol. Histol.* 35:595-601 (2004)). As used herein, "in situ hybridization" or "ISH" refers to a type of hybridization that uses a directly or indirectly labeled complementary DNA or RNA strand, such as a probe, to bind to and localize a specific nucleic acid, such as DNA or RNA, in a sample, in particular a portion or section of tissue or cells (in situ). The probe types can be double stranded DNA (dsDNA), single stranded DNA (ssDNA), single stranded complimentary RNA (ss-cRNA), messenger RNA (mRNA), micro RNA (miRNA), ribosomal RNA, mitochondrial RNA, and/or synthetic oligonucleotides. The term "fluorescent in situ hybridization" or "FISH" refers to a type of ISH utilizing a fluorescent label. The term "chromogenic in situ hybridization" or "CISH" refers to a type of ISH with a chromogenic label. ISH, FISH and CISH methods are well known to those skilled in the art (see, for example, Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000)).

For methods of the invention for in situ detection of nucleic acid targets in a cell, including but not limited to in situ hybridization or flow cytometry, the cell is optionally fixed and/or permeabilized before hybridization of the target probes. Fixing and permeabilizing cells can facilitate retaining the nucleic acid targets in the cell and permit the target probes, label probes, amplifiers, pre-amplifiers, pre-pre-amplifiers, and so forth, to enter the cell and reach the target nucleic acid molecule. The cell is optionally washed to remove materials not captured to a nucleic acid target. The cell can be washed after any of various steps, for example, after hybridization of the target probes to the nucleic acid targets to remove unbound target probes, after hybridization of the pre-pre-amplifiers, pre-amplifiers, amplifiers, and/or label probes to the target probes, and the like. Methods for fixing and permeabilizing cells for in situ detection of nucleic acids, as well as methods for hybridizing, washing and detecting target nucleic acids, are also well known in the art (see, for example, US 2008/0038725; US 2009/0081688; Hicks et al., *J. Mol. Histol.* 35:595-601 (2004); Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000); Shapiro, *Practical Flow Cytometry* 3rd ed., Wiley-Liss, New York (1995); Ormerod, *Flow Cytometry*, 2nd ed., Springer (1999)). Exemplary fixing agents include, but are not limited to, aldehydes (formaldehyde, glutaraldehyde, and the like), acetone, alcohols (methanol, ethanol, and the like). Exemplary permeabilizing agents include, but are not limited to, alcohols (methanol, ethanol, and the like), acids (glacial acetic acid, and the like), detergents (Triton, NP-40, Tween™ 20, and the like), saponin, digitonin, Leucoperm™ (BioRad, Hercules, CA), and enzymes (for example, lysozyme, lipases, proteases and peptidases). Permeabilization can also occur by mechanical disruption, such as in tissue slices.

For in situ detection of double stranded nucleic acids, generally the sample is treated to denature the double stranded nucleic acids in the sample to provide accessibility for the target probes to bind by hybridization to a strand of the target double stranded nucleic acid. Conditions for denaturing double stranded nucleic acids are well known in the art, and include heat and chemical denaturation, for example, with base (NaOH), formamide, dimethyl sulfoxide, and the like (see Wang et al., *Environ. Health Toxicol.* 29:e2014007 (doi: 10.5620/eht.2014.29.e2014007) 2014; Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, MD (1999)). For example, NaOH, LiOH or KOH, or other high pH buffers (pH>11) can be used to denature double stranded nucleic acids such as DNA. In addition, heat and chemical denaturation methods can be used in combination.

Such in situ detection methods can be used on tissue specimens immobilized on a glass slide, on single cells in suspension such as peripheral blood mononucleated cells (PBMCs) isolated from blood samples, and the like. Tissue specimens include, for example, tissue biopsy samples. Blood samples include, for example, blood samples taken for diagnostic purposes. In the case of a blood sample, the blood can be directly analyzed, such as in a blood smear, or the blood can be processed, for example, lysis of red blood cells, isolation of PBMCs or leukocytes, isolation of target cells, and the like, such that the cells in the sample analyzed by methods of the invention are in a blood sample or are derived from a blood sample. Similarly, a tissue specimen can be processed, for example, the tissue specimen minced and treated physically or enzymatically to disrupt the tissue into individual cells or cell clusters. Additionally, a cyto- logical sample can be processed to isolate cells or disrupt cell clusters, if desired. Thus, the tissue, blood and cyto- logical samples can be obtained and processed using meth- ods well known in the art. The methods of the invention can be used in diagnostic applications to identify the presence or absence of pathological cells based on the presence or absence of a nucleic acid target that is a biomarker indicative of a pathology.

It is understood by those skilled in the art that any of a number of suitable samples can be used for detecting target nucleic acids using methods of the invention. The sample for use in methods of the invention will generally be a biological sample or tissue sample. Such a sample can be obtained from a biological subject, including a sample of biological tissue or fluid origin that is collected from an individual or some other source of biological material such as biopsy, autopsy or forensic materials. A biological sample also includes samples from a region of a biological subject containing or suspected of containing precancerous or can- cer cells or tissues, for example, a tissue biopsy, including fine needle aspirates, blood sample or cytological specimen. Such samples can be, but are not limited to, organs, tissues, tissue fractions and/or cells isolated from an organism such as a mammal. Exemplary biological samples include, but are not limited to, a cell culture, including a primary cell culture, a cell line, a tissue, an organ, an organelle, a biological fluid, and the like. Additional biological samples include but are not limited to a skin sample, tissue biopsies, including fine needle aspirates, cytological samples, stool, bodily fluids, including blood and/or serum samples, saliva, semen, and the like. Such samples can be used for medical or veterinary diagnostic purposes. A sample can also be obtained from other sources, for example, food, soil, surfaces of objects, and the like, and other materials for which detection of target nucleic acids is desired. Thus, the methods of the invention can be used for detection of one or more pathogens, such as a virus, a bacterium, a fungus, a single celled organism such as a parasite, and the like, from a biological sample obtained from an individual or other sources.

Collection of cytological samples for analysis by methods of the invention are well known in the art (see, for example, Dey, "Cytology Sample Procurement, Fixation and Process- ing" in *Basic and Advanced Laboratory Techniques in Histopathology and Cytology* pp. 121-132, Springer, Singa- pore (2018); "Non-Gynocological Cytology Practice Guide- line" American Society of Cytopathology, Adopted by the ASC executive board Mar. 2, 2004). Methods for processing samples for analysis of cervical tissue, including tissue biopsy and cytology samples, are well known in the art (see, for example, *Cecil Textbook of Medicine*, Bennett and Plum, eds., 20th ed., WB Saunders, Philadelphia (1996); *Colpos- copy and Treatment of Cervical Intraepithelial Neoplasia: A Beginner's Manual*, Sellors and Sankaranarayanan, eds., International Agency for Research on Cancer, Lyon, France (2003); Kalaf and Cooper, *J. Clin. Pathol.* 60:449-455 (2007); Brown and Trimble, *Best Pract. Res. Clin. Obstet. Gynaecol.* 26:233-242 (2012); Waxman et al., *Obstet. Gyne- col.* 120:1465-1471 (2012); *Cervical Cytology Practice Guidelines TOC*, Approved by the American Society of Cytopathology (ASC) Executive Board, Nov. 10, 2000)). In one embodiment, the cytological sample is a cervical sample, for example, a pap smear. In one embodiment, the sample is a fine needle aspirate.

In particular embodiments of the invention, the sample is a tissue specimen or is derived from a tissue specimen. In other particular embodiments of the invention, the sample is a blood sample or is derived from a blood sample. In still other particular embodiments of the invention, the sample is a cytological sample or is derived from a cytological sample.

The invention is based on building a complex between a target nucleic acid in order to label the target nucleic acid with a detectable label. Such a complex is sometimes referred to as a signal generating complex (SGC; see, for example, US 20170101672). Such a complex, or SGC, is achieved by building layers of molecules that allow the attachment of a large number of labels to a target nucleic acid.

The methods of the invention can employ a signal gen- erating complex (SGC), where the SGC comprises multiple molecules rather than a single molecule. Such an SGC is particularly useful for amplifying the detectable signal, providing higher sensitivity detection of target nucleic acids. Such methods for amplifying a signal are described, for example, in U.S. Pat. Nos. 5,635,352, 5,124,246, 5,710,264, 5,849,481, and 7,709,198, and U.S. publications 2008/ 0038725 and 2009/0081688, as well as WO 2007/001986 and WO 2012/054795, each of which is incorporated herein by reference. The generation of an SGC is a principle of the RNAscope™ assay (see U.S. Pat. Nos. 7,709,198, 8,658,361 and 9,315,854, U.S. publications 2008/0038725, 2009/ 0081688 and 2016/0201117, as well as WO 2007/001986 and WO 2012/054795, each of which is incorporated herein by reference).

Figures 6A, 6B, 6C:
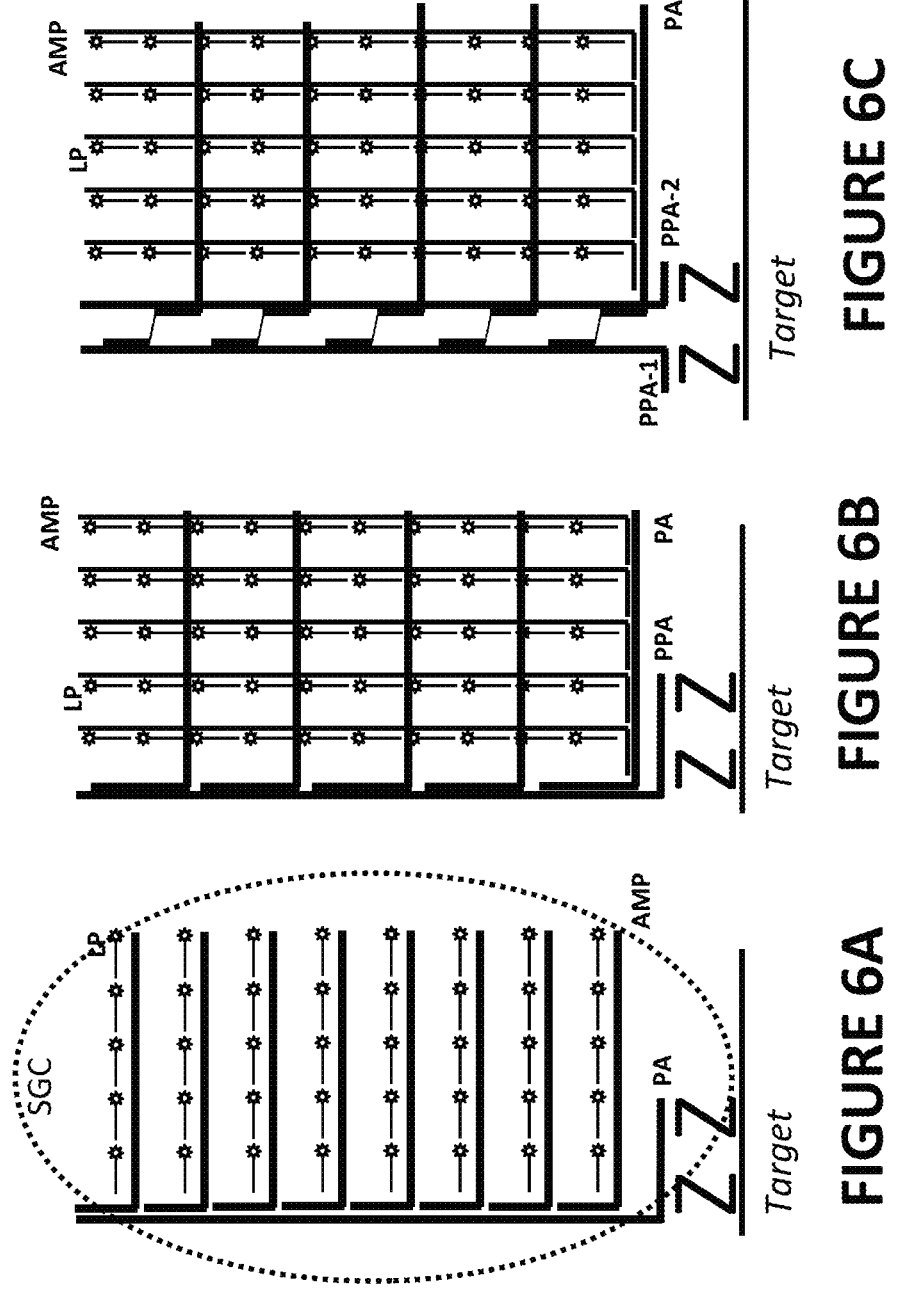
FIGS. 6A-6C show a schematic of previously described methods of detecting a nucleic acid target using a signal generating complex (SGC). PPA, pre-pre-amplifier; PA, pre-amplifier; AMP, amplifier; LP, label probe.

A basic Signal Generating Complex (SGC) is illustrated in FIG. 6A (see also US 2009/0081688, which is incorpo- rated herein by reference). A pair of target probes, depicted in FIG. 6 as a pair of "Z's", hybridizes to a complementary molecule sequence, labeled "Target". Each target probe contains an additional sequence complementary to a pre- amplifier molecule (PA), which must hybridize simultane- ously to both members of the target probe pair in order to bind stably. The pre-amplifier molecule is made up of two domains: one domain with a region that hybridizes to each target probe, and one domain that contains a series of nucleotide sequence repeats, each complementary to a sequence on the amplifier molecule (Amp). The presence of multiple repeats of this sequence allows multiple amplifier molecules to hybridize to one pre-amplifier, which increases the overall signal amplification. Each amplifier molecule is made up of two domains, one domain with a region that hybridizes to the pre-amplifier, and one domain that contains a series of nucleotide sequence repeats, each complementary to a sequence on the label probe (LP), allowing multiple label probes to hybridize to each amplifier molecule, further increasing the total signal amplification. Each label probe contains two components. One component is made up of a nucleotide sequence complementary to the repeat sequence on the amplifier molecule to allow the label probe to hybridize. This nucleotide sequence is linked to the second component, which can be any signal-generating entity, including a fluorescent or chromogenic label for direct visualization, a directly detectable metal isotope, or an enzyme or other chemical capable of facilitating a chemical reaction to generate a fluorescent, chromogenic, or other detectable signal, as described herein. In FIG. 6A, the label probe is depicted as a line, representing the nucleic acid component, and a star, representing the signal-generating component. Together, the assembly from target probe to label probe is referred to as a Signal Generating Complex (SGC).

FIG. 6B illustrates a SGC enlarged by adding an amplification molecule layer, in this case a pre-pre-amplifier molecule (PPA). The PPA binds to both target probes in one domain and multiple pre-amplifiers (PAs) in another domain.

FIG. 6C illustrates a different SGC structure that uses collaborative hybridization at the pre-amplifier level (see US 2017/0101672, which is incorporated herein by reference). Similarly to the SGC formed in FIGS. 6A and 6B, a pair of target probes hybridize to the target molecule sequence. Each target probe contains an additional sequence complementary to a unique pre-pre-amplifier molecule (PPA-1; PPA-2). The use of two independent molecules sets up a base on which collaborative hybridization can be required. Each pre-pre-amplifier molecule is made up of two domains, one domain with a region that hybridizes to one of the target probes, and one domain that contains a series of nucleotide sequence repeats, each containing both a sequence complementary to a sequence within the pre-amplifier molecule (PA), as well as a spacer sequence to facilitate PPA-PA binding efficiency. To stably attach to the growing SGC, each PA must hybridize to both PPA molecules simultaneously. Each pre-amplifier molecule is made up of two domains, one domain that contains sequences complementary to both pre-pre-amplifiers to allow hybridization, and one domain that contains a series of nucleotide sequence repeats each complementary to a sequence on the amplifier molecule (AMP). Multiple repeats of the amplifier hybridization sequence allows multiple amplifier molecules to hybridize to each pre-amplifier, further increasing signal amplification. For simplicity of illustration, amplifier molecules are shown hybridizing to one pre-amplifier molecule, but it is understood that amplifiers can bind to each pre-amplifier. Each amplifier molecule contains a series of nucleotide sequence repeats complementary to a sequence within the label probe (LP), allowing several label probes to hybridize to each amplifier molecule. Each label probe contains a signal-generating element to provide for signal detection.

Figure 3C:
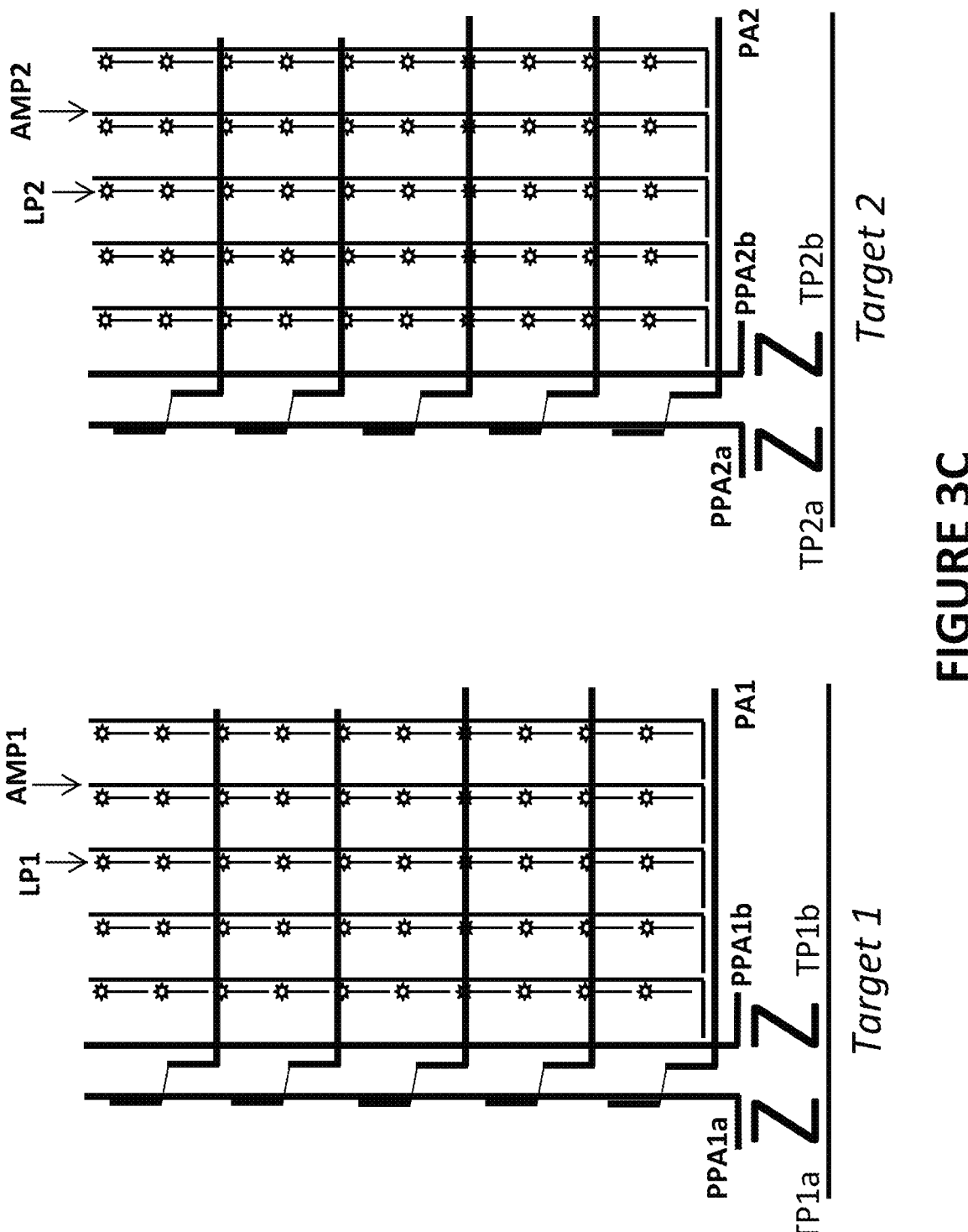

As described above, whether using a configuration as depicted in FIG. 3A, 3B, 6A or 6B, or a configuration as depicted in FIGS. 3C and 6C, the components of the SGC are designed such that the binding of both target probes is required in order to build an SGC. In the case of the configuration of FIG. 3A, 3B, 6A or 6B, a pre-amplifier (or pre-pre-amplifier in FIGS. 3B and 6B) must bind to both members of the target probe pair for stable binding to occur. This is achieved by designing binding sites between the target probes and the pre-amplifier (or pre-pre-amplifier) such that binding of both target probes to the pre-amplifier (or pre-pre-amplifier) has a higher melting temperature (Tm) than the binding of a single target probe to the pre-amplifier (or pre-pre-amplifier), and where the binding of a single target probe is unstable under the conditions of the assay. This design has been described previously, for example, in U.S. Pat. No. 7,709,198, U.S. publications 2008/0038725 and 2009/0081688, WO 2007/001986 WO 2007/002006, Wang et al., supra, 2012, Anderson et al., supra, 2016). By configuring the SGC components this way, the assembly of the SGC is achieved when both target probes are bound to the target nucleic acid and the pre-amplifier, thereby reducing background noise since assembly of an SGC as a false positive is minimized.

In the case of the configuration of FIGS. 3C and 6C, the requirement that an SGC be formed only when both members of a target probe pair are bound to the target nucleic acid is achieved by requiring that a pre-amplifier be bound to both pre-pre-amplifiers, which in turn are bound to both members of the target probe pair, respectively. This requirement is achieved by designing the binding sites between the pre-pre-amplifiers and the pre-amplifier such that the melting temperature (Tm) between the binding of both pre-pre-amplifiers to the pre-amplifier is higher than the melting temperature of either pre-pre-amplifier alone, and where the binding of one of the pre-pre-amplifiers to the pre-amplifier is unstable under the conditions of the assay. This design has been described previously, for example, in US 20170101672, WO 2017/066211 and Baker et al., supra, 2017). Unless the pre-amplifier is bound to both pre-pre-amplifiers, the amplifiers and label probes cannot assemble into an SGC bound to the target nucleic acid, thereby reducing background noise since assembly of an SGC as a false positive is minimized.

As disclosed herein, the methods of the invention can be based on building a signal-generating complex (SGC) bound to a target nucleic acid in order to detect the presence of the target nucleic acid in the cell. The components for building an SGC generally comprise nucleic acids such that nucleic acid hybridization reactions are used to bind the components of the SGC to the target nucleic acid. Methods of selecting appropriate regions and designing specific and selective reagents that bind to the target nucleic acids, in particular oligonucleotides or probes that specifically and selectively bind to a target nucleic acid, or other components of the SGC, are well known to those skilled in the art (see Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, MD (1999)). The target probes are designed such that the probes specifically hybridize to a target nucleic acid. A desired specificity can be achieved using appropriate selection of regions of a target nucleic acid as well as appropriate lengths of a binding agent such as an oligonucleotide or probe, and such selection methods are well known to those skilled in the art. One skilled in the art will readily understand and can readily determine appropriate reagents, such as oligonucleotides or probes, that can be used to target one particular target nucleic acid over another target nucleic acid or over non-target nucleic acids, or to provide binding to the components of the SGC. Thus, it is understood that "specifically hybridize," "specifically label," and "specifically bind" (or grammatical variations thereof), refer to hybridization, labeling or binding to a target nucleic acid but not to non-target nucleic acids, for example, another target nucleic acid or nucleic acids that are not desired to be targeted. Similar specificity can be achieved for a target-specific SGC by using appropriate selection of unique sequences such that a given component of a target-specific SGC (for example, target probe, pre-pre-amplifier, pre-amplifier, amplifier, label probe) will bind to the respective components such that the target-specific SGC is bound to a specific target and not to another target nucleic acid (see FIG. 3).

As described herein, embodiments of the invention include the use of target probe pairs. In the case where a pair of target probes binds to the same pre-amplifier (FIGS. 3A and 6A) or pre-pre-amplifier (FIGS. 3B and 6B), a probe configuration, sometimes referred to as a "Z" configuration, can be used. Such a configuration and its advantages for increasing sensitivity and decreasing background are described, for example, in U.S. Pat. No. 7,709,198, U.S. publications 2008/0038725 and 2009/0081688, and WO 2007/001986 and WO 2007/002006, each of which is incorporated herein by reference. U.S. Pat. No. 7,709,198 and U.S. publications 2008/0038725 and 2009/0081688 additionally describe details for selecting characteristics of the target probes, such as target probe pairs, including length, orientation, hybridization conditions, and the like. One skilled in the art can readily identify suitable configurations based on the teachings herein and, for example, in U.S. Pat. No. 7,709,198, U.S. publications 2008/0038725 and 2009/0081688, and WO 2007/001986 and WO 2007/002006.

As described herein, the target binding site of the target probes in a target probe pair can be in any desired orientation and combination. For example, the target binding site of one member of the target probe pair can be 5' or 3' to the pre-amplifier or pre-pre-amplifier binding site, and the other member of the pair can independently be oriented with the target binding site 5' or 3' to the pre-amplifier or pre-pre-amplifier binding site.

In another embodiment, the SGC used to detect the presence of a target nucleic acid is based on a collaborative hybridization of one or more components of the SGC (see US 20170101672 and WO 2017/066211, each of which is incorporated herein by reference). Such a collaborative hybridization is also referred to herein as BaseScope™. In a collaborative hybridization effect, the binding between two components of an SGC is mediated by two binding sites, and the melting temperature of the binding to the two sites simultaneously is higher than the melting temperature of the binding of one site alone (see US 20170101672 and WO 2017/066211). The collaborative hybridization effect can be enhanced by target probe set configurations as described in US 20170101672 and WO 2017/066211.

The methods of the invention, and related compositions, can utilize collaborative hybridization to increase specificity and to reduce background in in situ detection of nucleic acid targets, where a complex physiochemical environment and the presence of an overwhelming number of non-target molecules can generate high noise. Using such a collaborative hybridization method, the binding of label probes only occurs when the SGC is bound to the target nucleic acid. As described in US 20170101672 and WO 2017/066211 and illustrated in FIG. 1 thereof, the method can be readily modified to provide a desired signal to noise ratio by increasing the number of collaborative hybridizations in one or more components of the SGC.

In another embodiment, the collaborative hybridization can be applied to various components of the SGC. For example, the binding between components of an SGC can be a stable reaction, as described herein, or the binding can be configured to require a collaborative hybridization, also as described herein. In such a case, the binding component intended for collaborative hybridization are designed such that the component contains two segments that bind to another component.

Thus, the methods for detecting a target nucleic acid can utilize collaborative hybridization for the binding reactions between any one or all of the components in the detection system that provides an SGC specifically bound to a target nucleic acid. The number of components, and which components, to apply collaborative hybridization can be selected based on the desired assay conditions, the type of sample being assayed, a desired assay sensitivity, and so forth. Any one or combination of collaborative hybridization binding reactions can be used to increase the sensitivity and specificity of the assay. In embodiments of the invention, the collaborative hybridization can be between a pre-pre-amplifier and a pre-amplifier, between a pre-amplifier and an amplifier, between an amplifier and a label probe, or combinations thereof (see, for example, US 20170101672 and WO 2017/066211).

As disclosed herein, the components are generally bound directly to each other. In the case of nucleic acid containing components, the binding reaction is generally by hybridization. In the case of a hybridization reaction, the binding between the components is direct. If desired, an intermediary component can be included such that the binding of one component to another is indirect, for example, the intermediary component contains complementary binding sites to bridge two other components.

As described herein, the configuration of various components can be selected to provide a desired stable or collaborative hybridization binding reaction (see, for example, US 20170101672). It is understood that, even if a binding reaction is exemplified herein as a stable or unstable reaction, such as for a collaborative hybridization, any of the binding reactions can be modified, as desired, so long as the target nucleic acid is detected. It is further understood that the configuration can be varied and selected depending on the assay and hybridization conditions to be used. In general, if a binding reaction is desired to be stable, the segments of complementary nucleic acid sequence between the components is generally in the range of 10 to 50 nucleotides, or greater, for example, 16 to 30 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, or greater. If a binding reaction is desired to be relatively unstable, such as when a collaborative hybridization binding reaction is employed, the segments of complementary nucleic acid sequence between the components is generally in the range of 5 to 18 nucleotides, for example, 5, 6, 7, 8, 9, 10, 11, 12, 13, 14, 15, 16, 17 or 18 nucleotides. It is understood that the nucleotide lengths can be somewhat shorter or longer for a stable or unstable hybridization, depending on the sequence (for example, GC content) and the conditions employed in the assay. It is further understood, as disclosed herein, that modified nucleotides such as Locked Nucleic Acid (LNA) or Bridged Nucleic Acid (BNA) can be used to increase the binding strength at the modified base, thereby allowing length of the binding segment to be reduced. Thus, it is understood that, with respect to the length of nucleic acid segments that are complementary to other nucleic acid segments, the lengths described herein can be reduced further, if desired. A person skilled in the art can readily determine appropriate probe designs, including length, the presence of modified nucleotides, and the like, to achieve a desired interaction between nucleic acid components.

In designing binding sites between two nucleic acid sequences comprising complementary sequences, the complementary sequences can optionally be designed to maximize the difference in melting temperature ($dT_m$). This can be done by using melting temperature calculation algorithms known in the art (see, for example, SantaLucia, *Proc. Natl. Acad. Sci. U.S.A.* 95:1460-1465 (1998)). In addition, artificial modified bases such as Locked Nucleic Acid (LNA) or bridged nucleic acid (BNA) and naturally occurring 2'-O-methyl RNA are known to enhance the binding strength between complementary pairs (Petersen and Wengel, *Trends Biotechnol.* 21:74-81 (2003); Majlessi et al., *Nucl. Acids Res.* 26:2224-2229 (1998)). These modified bases can be strategically introduced into the binding site between components of an SGC, as desired.

One approach is to utilize modified nucleotides (LNA, BNA or 2'-O-methyl RNA). Because each modified base can increase the melting temperature, the length of binding regions between two nucleic acid sequences (i.e., complementary sequences) can be substantially shortened. The binding strength of a modified base to its complement is stronger, and the difference in melting temperatures ($dT_m$) is increased. Yet another embodiment is to use three modified bases (for example, three LNA, BNA or 2'-O-methyl RNA bases, or a combination of two or three different modified bases) in the complementary sequences of a nucleic acid component or between two nucleic acid components, for example of a signal generating complex (SGC), that are to be hybridized. Such components can be, for example, a pre-pre-amplifier, a pre-amplifier, an amplifier, a label probe, or a pair of target probes.

The modified bases, such as LNA or BNA, can be used in the segments of selected components of SGC, in particular those mediating binding between nucleic acid components, which increases the binding strength of the base to its complementary base, allowing a reduction in the length of the complementary segments (see, for example, Petersen and Wengel, *Trends Biotechnol.* 21:74-81 (2003); U.S. Pat. No. 7,399,845). Artificial bases that expand the natural 4-letter alphabet such as the Artificially Expanded Genetic Information System (AEGIS; Yang et al., *Nucl. Acids Res.* 34 (21): 6095-6101 (2006)) can be incorporated into the binding sites among the interacting components of the SGC. These artificial bases can increase the specificity of the interacting components, which in turn can allow lower stringency hybridization reactions to yield a higher signal.

With respect to a target probe pair, the target probe pair can be designed to bind to immediately adjacent segments of the target nucleic acid or on segments that have one to a number of bases between the target probe binding sites of the target probe pair. Generally, target probe pairs are designed for binding to the target nucleic acid such that there are generally between 0 to 500 bases between the binding sites on the target nucleic acid, for example, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 420, 440, 460, 480, or 500 bases, or any integer length in between. In particular embodiments, the binding sites for the pair of target probes are between 0 to 100, 0 to 200, or 0 to 300 bases, or any integer length in between. In the case where more than one target probe pair is used in a target probe set to bind to the same target nucleic acid that is RNA or single stranded DNA, and where there is a gap in the binding sites between a pair of target probes, it is understood that the binding sites of different target probe pairs do not overlap. In the case of detecting double stranded nucleic acids, such as DNA, some overlap between different target probe pairs can occur, so long as the target probe pairs are able to concurrently bind to the respective binding sites of the double stranded target nucleic acid.

The SGC also comprises a plurality of label probes (LPs). Each LP comprises a segment that is detectable. The detectable component can be directly attached to the LP, or the LP can hybridize to another nucleic acid that comprises the detectable component, i.e. the label. As used herein, a "label" is a moiety that facilitates detection of a molecule. Common labels in the context of the present invention include fluorescent, luminescent, light-scattering, and/or colorimetric labels. Suitable labels include enzymes, and fluorescent and chromogenic moieties, as well as radionuclides, substrates, cofactors, inhibitors, chemiluminescent moieties, magnetic particles, rare earth metals, metal isotopes, and the like. In a particular embodiment of the invention, the label is an enzyme. Exemplary enzyme labels include, but are not limited to Horse Radish Peroxidase (HRP), Alkaline Phosphatase (AP), β-galactosidase, glucose oxidase, and the like, as well as various proteases. Other labels include, but are not limited to, fluorophores, Dinitrophenyl (DNP), and the like. Labels are well known to those skilled in the art, as described, for example, in Hermanson, *Bioconjugate Techniques*, Academic Press, San Diego (1996), and U.S. Pat. Nos. 3,817,837; 3,850,752; 3,939,350; 3,996,345; 4,277,437; 4,275,149; and 4,366,241. Many labels are commercially available and can be used in methods and assays of the invention, including detectable enzyme/substrate combinations (Pierce, Rockford IL; Santa Cruz Biotechnology, Dallas TX; Life Technologies, Carlsbad CA). In a particular embodiment of the invention, the enzyme can utilize a chromogenic or fluorogenic substrate to produce a detectable signal, as described herein. Exemplary labels are described herein.

Any of a number of enzymes or non-enzyme labels can be utilized so long as the enzymatic activity or non-enzyme label, respectively, can be detected. The enzyme thereby produces a detectable signal, which can be utilized to detect a target nucleic acid. Particularly useful detectable signals are chromogenic or fluorogenic signals. Accordingly, particularly useful enzymes for use as a label include those for which a chromogenic or fluorogenic substrate is available. Such chromogenic or fluorogenic substrates can be converted by enzymatic reaction to a readily detectable chromogenic or fluorescent product, which can be readily detected and/or quantified using microscopy or spectroscopy. Such enzymes are well known to those skilled in the art, including but not limited to, horseradish peroxidase, alkaline phosphatase, β-galactosidase, glucose oxidase, and the like (see Hermanson, *Bioconjugate Techniques*, Academic Press, San Diego (1996)). Other enzymes that have well known chromogenic or fluorogenic substrates include various peptidases, where chromogenic or fluorogenic peptide substrates can be utilized to detect proteolytic cleavage reactions. The use of chromogenic and fluorogenic substrates is also well known in bacterial diagnostics, including but not limited to the use of α- and β-galactosidase, β-glucuronidase, 6-phospho-β-D-galatoside 6-phosphogalactohydrolase, β-gluosidase, α-glucosidase, amylase, neuraminidase, esterases, lipases, and the like (Manafi et al., *Microbiol. Rev.* 55:335-348 (1991)), and such enzymes with known chromogenic or fluorogenic substrates can readily be adapted for use in methods of the present invention.

Various chromogenic or fluorogenic substrates to produce detectable signals are well known to those skilled in the art and are commercially available. Exemplary substrates that can be utilized to produce a detectable signal include, but are not limited to, 3,3'-diaminobenzidine (DAB), 3,3',5,5'-tetramethylbenzidine (TMB), Chloronaphthol (4-CN)(4-chloro-1-naphthol), 2,2'-azino-bis(3-ethylbenzothiazoline-6-sulphonic acid) (ABTS), o-phenylenediamine dihydrochloride (OPD), and 3-amino-9-ethylcarbazole (AEC) for horseradish peroxidase; 5-bromo-4-chloro-3-indolyl-1-phosphate (BCIP), nitroblue tetrazolium (NBT), Fast Red (Fast Red TR/AS-MX), and p-Nitrophenyl Phosphate (PNPP) for alkaline phosphatase; 1-Methyl-3-indolyl-β-D-galactopyranoside and 2-Methoxy-4-(2-nitrovinyl)phenyl β-D-galactopyranoside for β-galactosidase; 2-Methoxy-4-(2-nitrovinyl)phenyl β-D-glucopyranoside for β-glucosidase; and the like. Exemplary fluorogenic substrates include, but are not limited to, 4-(Trifluoromethyl) umbelliferyl phosphate for alkaline phosphatase; 4-Methylumbelliferyl phosphate bis (2-amino-2-methyl-1,3-propanediol), 4-Methylumbelliferyl phosphate bis (cyclohexylammonium) and 4-Methylumbelliferyl phosphate for phosphatases; QuantaBlu™ and QuantaRed™ for horseradish peroxidase; 4-Methylumbelliferyl β-D-galactopyranoside, Fluorescein di(β-D-galactopyranoside) and Naphthofluorescein di-(β-D-galactopyranoside) for β-galactosidase; 3-Acetylumbelliferyl β-D-glucopyranoside and 4-Methylumbelliferyl-β-D-glucopyranoside for β-glucosidase; and 4-Methylumbelliferyl-α-D-galactopyranoside for α-galactosidase. Exemplary enzymes and substrates for producing a detectable signal are also described, for example, in US publication 2012/0100540. Various detectable enzyme substrates, including chromogenic or fluorogenic substrates, are well known and commercially available (Pierce, Rockford IL; Santa Cruz Biotechnology, Dallas TX; Invitrogen, Carlsbad CA; 42 Life Science; Biocare). Generally, the substrates are converted to products that form precipitates that are deposited at the site of the target nucleic acid. Other exemplary substrates include, but are not limited to, HRP-Green (42 Life Science), Betazoid DAB, Cardassian DAB, Romulin AEC, Bajoran Purple, Vina Green, Deep Space Black™, Warp Red™, Vulcan Fast Red and Ferangi Blue from Biocare (Concord CA; biocare.net/products/detection/chromogens).

Exemplary rare earth metals and metal isotopes suitable as a detectable label include, but are not limited to, lanthanide (III) isotopes such as 141Pr, 142Nd, 143Nd, 144Nd, 145Nd, 146Nd, 147Sm, 148Nd, 149Sm, 150Nd, 151Eu, 152Sm, 153Eu, 154Sm, 155Gd, 156Gd, 158Gd, 159Tb, 160Gd, 161Dy, 162Dy, 163Dy, 164Dy, 165Ho, 166Er, 167Er, 168Er, 169Tm, 170Er, 171Yb, 172Yb, 173Yb, 174Yb, 175Lu, and 176Yb. Metal isotopes can be detected, for example, using time-of-flight mass spectrometry (TOF-MS) (for example, Fluidigm Helios and Hyperion systems, fluidigm.com/systems; South San Francisco, CA).

Biotin-avidin (or biotin-streptavidin) is a well known signal amplification system based on the fact that the two molecules have extraordinarily high affinity to each other and that one avidin/streptavidin molecule can bind four biotin molecules. Antibodies are widely used for signal amplification in immunohistochemistry and ISH. Tyramide signal amplification (TSA) is based on the deposition of a large number of haptenized tyramide molecules by peroxidase activity. Tyramine is a phenolic compound. In the presence of small amounts of hydrogen peroxide, immobilized Horse Radish Peroxidase (HRP) converts the labeled substrate into a short-lived, extremely reactive intermediate. The activated substrate molecules then very rapidly react with and covalently bind to electron-rich moieties of proteins, such as tyrosine, at or near the site of the peroxidase binding site. In this way, many hapten molecules conjugated to tyramide can be introduced at the hybridization site in situ. Subsequently, the deposited tyramide-hapten molecules can be visualized directly or indirectly. Such a detection system is described in more detail, for example, in U.S. publication 2012/0100540.

Embodiments described herein can utilize enzymes to generate a detectable signal using appropriate chromogenic or fluorogenic substrates. It is understood that, alternatively, a label probe can have a detectable label directly coupled to the nucleic acid portion of the label probe. Exemplary detectable labels are well known to those skilled in the art, including but not limited to chromogenic or fluorescent labels (see Hermanson, *Bioconjugate Techniques*, Academic Press, San Diego (1996)). Exemplary fluorophores useful as labels include, but are not limited to, rhodamine derivatives, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like; 7-nitrobenz-2-oxa-1,3-diazole (NBD); fluorescein and derivatives thereof; napthalenes such as dansyl (5-dimethylaminonapthalene-1-sulfonyl); coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like; 4,4-difluoro-4-bora-3a,4a-diaza-s-indacene (BODIPY™) and derivatives thereof (Molecular Probes; Eugene, OR); pyrenes and sulfonated pyrenes such as Cascade Blue™ and derivatives thereof, including 8-methoxy-pyrene-1,3,6-trisulfonic acid, and the like; pyridyloxazole derivatives and dapoxyl derivatives (Molecular Probes); Lucifer Yellow (3,6-disulfonate-4-amino-naphthalimide) and derivatives thereof; CyDye™ fluorescent dyes (Amersham/GE Healthcare Life Sciences; Piscataway NJ), ATTO 390, DyLight 395XL, ATTO 425, ATTO 465, ATTO 488, ATTO 490LS, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 643, ATTO 647, ATTO 647N, ATTO 655, ATTO Oxa12, ATTO 665, ATTO 680, ATTO 700, ATTO 725, ATTO 740, Cyan 500 NETS-Ester (ATTO-TECH, Siegen, Germany), and the like. Exemplary chromophores include, but are not limited to, phenolphthalein, malachite green, nitroaromatics such as nitrophenyl, diazo dyes, dabsyl (4-dimethylaminoazobenzene-4'-sulfonyl), and the like.

As disclosed herein, the methods of the invention can utilize concurrent detection of multiple target nucleic acids. In the case of using fluorophores as labels, the fluorophores to be used for detection of multiple target nucleic acids are selected so that each of the fluorophores are distinguishable and can be detected concurrently in the fluorescence microscope in the case of concurrent detection of target nucleic acids. Such fluorophores are selected to have spectral separation of the emissions so that distinct labeling of the target nucleic acids can be detected concurrently. Methods of selecting suitable distinguishable fluorophores for use in methods of the invention are well known in the art (see, for example, Johnson and Spence, "*Molecular Probes Handbook, a Guide to Fluorescent Probes and Labeling Technologies*, 11th ed., Life Technologies (2010)).

Well known methods such as microscopy, cytometry (e.g., mass cytometry, cytometry by time of flight (CyTOF), flow cytometry), or spectroscopy can be utilized to visualize chromogenic, fluorescent, or metal detectable signals associated with the respective target nucleic acids. In general, either chromogenic substrates or fluorogenic substrates, or chromogenic or fluorescent labels, or rare earth metal isotopes, will be utilized for a particular assay, if different labels are used in the same assay, so that a single type of instrument can be used for detection of nucleic acid targets in the same sample.

As disclosed herein, the label probes can be designed such that the labels are optionally cleavable. As used herein, a cleavable label refers to a label that is attached or conjugated to a label probe so that the label can be removed from an SGC, for example, in order to use the same label in a subsequent round of labeling and detecting of target nucleic acids. Generally, the labels are conjugated to the label probe by a chemical linker that is cleavable. Methods of conjugating a label to a label probe so that the label is cleavable are well known to those skilled in the art (see, for example, Hermanson, *Bioconjugate Techniques*, Academic Press, San Diego (1996); Daniel et al., BioTechniques 24(3):484-489 (1998)). One particular system of labeling oligonucleotides is the FastTag™ system (Daniel et al., supra, 1998; Vector Laboratories, Burlinghame CA). Various cleavable moieties can be included in the linker so that the label can be cleaved from the label probe. Such cleavable moieties include groups that can be chemically, photo chemically or enzymatically cleaved. Cleavable chemical linkers can include a cleavable chemical moiety, such as disulfides, which can be cleaved by reduction, glycols or diols, which can be cleaved by periodate, diazo bonds, which can be cleaved by dithionite, esters, which can be cleaved by hydroxylamine, sulfones, which can be cleaved by base, and the like (see Hermanson, supra, 1996). One particularly useful cleavable linker is a linker containing a disulfide bond, which can be cleaved by reducing the disulfide bond. In other embodiments, the linker can include a site for cleavage by an enzyme. For example, the linker can contain a proteolytic cleavage site. Generally, such a cleavage site is for a sequence-specific protease. Such proteases include, but are not limited to, human rhinovirus 3C protease (cleavage site LEVLFQ/GP; SEQ ID NO:1), enterokinase (cleavage site DDDDK/; SEQ ID NO:2), factor Xa (cleavage site IEGR/; SEQ ID NO:3), tobacco etch virus protease (cleavage site ENLYFQ/G; SEQ ID NO:4), and thrombin (cleavage site LVPR/GS; SEQ ID NO:5) (see, for example, Oxford Genetics, Oxford, UK). Another cleavable moiety can be, for example, uracil-DNA (DNA containing uracil), which can be cleaved by uracil-DNA glycosylase (UNG) (see, for example, Sidorenko et al., *FEBS Lett.* 582(3):410-404 (2008)).

The invention relates to using cleavable labels such that the labels bound to target nucleic acids can be removed from the target nucleic acid. As disclosed herein, on the last round of detection, the labels can optionally be cleavable, as cleavage of the labels is not required on the last round of detection. The cleavable labels can be removed by applying an agent, such as a chemical agent or light, to cleave the label and release it from the label probe. As discussed above, useful cleaving agents for chemical cleavage include, but are not limited to, reducing agents, periodate, dithionite, hydroxylamine, base, and the like (see Hermanson, supra, 1996). One useful method for cleaving a linker containing a disulfide bond is the use of tris(2-carboxyethyl)phosphine (TCEP) (see Moffitt et al., *Proc. Natl. Acad. Sci.* USA 113:11046-11051 (2016)). In one embodiment, TCEP is used as an agent to cleave a label from a label probe.

In another embodiment, instead of using cleavable labels, the label probes bound to the SGC can be selectively removed, or washed off, by exposing the SGCs attached to the target nucleic acids at a temperature that is higher than the Tm of the label probe-amplifier binding sequence. Methods for selectively removing a component of the SGC, such as removing label probes bound to amplifiers in the SGC, by selecting suitable temperatures and conditions to disrupt the binding between the label probes and the amplifiers in the SGCs are well known in the art and disclosed herein. In the case of using selective removal of the label probes from the SGC, the components of the SGC are designed such that interactions of other components of the SGC besides the label probe-amplifier interaction remain stable during the conditions of disruption of the label probe binding to the amplifier. Similar to the use of a label probe comprising a cleavable label, it is understood that, on the final iterative round of detection, it is not necessary for the melting temperature between the label probes and the amplifiers to be lower than the melting temperature between the target probes, pre-pre-amplifiers (if used), pre-amplifiers and amplifiers since no further rounds of detection are to be made. Thus, on the final iterative round of detection, it is optional for the melting temperature between the label probes and the amplifiers to be lower than the melting temperature between the target probes, pre-pre-amplifiers (if used), pre-amplifiers and amplifiers, such that the label probe and label remain bound to the SGC on the final iterative round of detection.

The invention described herein generally relates to detection of multiple target nucleic acids in a sample. It is understood that the methods of the invention can additionally be applied to detecting multiple target nucleic acids and optionally other molecules in the sample, in particular in the same cell as the target nucleic acid. For example, in addition to detecting multiple target nucleic acids, proteins expressed in a cell can also concurrently be detected using a similar rationale as described herein for detecting target nucleic acids. In this case, in one or more rounds of detection of multiple target nucleic acids, and optionally one or more proteins expressed in a cell can be detected, for example, by using a detectable label to detect the protein. If the protein is being detected in an earlier round of target nucleic acid detection, the protein can be detected with a cleavable label, similar to that used for detecting target nucleic acids. If the protein is being detected in the last round of detection, the label does not need to be cleavable. Detection of proteins in a cell are well known to those skilled in the art, for example, by detecting the binding of protein-specific antibodies using any of the well known detection systems, including those described herein for detection of target nucleic acids. Detection of target nucleic acids and protein in the same cell is described in the Examples (see also Schulz et al., *Cell Syst.* 6(1):25-36 (2018)).

It is understood that the invention can be carried out in any desired order, so long as the target nucleic acids are detected. Thus, in a method of the invention, the steps of contacting a cell with any components for assembly of an SGC can be performed in any desired order, can be carried out sequentially, or can be carried out simultaneously, or some steps can be performed sequentially while others are performed simultaneously, as desired, so long as the target nucleic acids are detected. It is further understood that embodiments disclosed herein can be independently combined with other embodiments disclosed herein, as desired, in order to utilize various configurations, component sizes, assay conditions, assay sensitivity, and the like.

It is understood that the invention can be carried out in any format that provides for the detection of a target nucleic acid. Although implementation of the invention has generally been described herein using in situ hybridization, it is understood that the invention can be carried out for detection of target nucleic acids in other formats, in particular for detection of target nucleic acids in a cell, as are well known in the art. One method that can be used for detecting target nucleic acids in a cell is flow cytometry, as is well known in the art (see, for example, Shapiro, *Practical Flow Cytometry* 3rd ed., Wiley-Liss, New York (1995); Ormerod, *Flow Cytometry*, 2nd ed., Springer (1999)). The methods, samples and kits of the invention can thus be used in an in situ hybridization assay format or another format, such as flow cytometry. The application of nucleic acid detection methods, including in situ hybridization, to flow cytometry has been described previously (see, for example, Hanley et al.,

*PLoS One,* 8(2):e57002. doi: 10.1371/journal.pone.0057002 (2013); Baxter et al., *Nature Protocols* 12(10):2029-2049 (2017)).

In some cases, it can be desirable to reduce the number of assay steps, for example, reduce the number of hybridization and wash steps. One way of reducing the number of assay steps is to pre-assemble some or all components of the SGC prior to contacting with a cell. Such a pre-assembly can be performed by hybridizing some or all of the components of the SGC together prior to contacting the target nucleic acid.

The invention also provides a sample comprising a cell or a plurality of cells. The cell can optionally be fixed. The cells can optionally be permeabilized. Fixing and/or permeabilizing cells is particularly applicable to in situ hybridization assays.

The invention additionally provides a slide comprising a cell or a plurality of cells. Optionally, the cell or cells are fixed to the slide. Optionally, the cell or cells are permeabilized. In particular embodiments, the cells on the slide are fixed and/or permeabilized for an in situ assay.

The invention also provides a kit comprising the components of an SGC, as described herein, where the kit does not include the target nucleic acid. Such a kit can comprise pre-amplifiers (PAs), amplifiers (AMPs) and label probes (LPs), and optionally pre-pre-amplifiers (PPAs), as disclosed herein. Optionally the kit can comprise target probes (TPs) directed to a particular target nucleic acid, or a plurality of target nucleic acids. The components of a kit of the invention can optionally be in a container, and optionally instructions for using the kit can be provided.

It is understood that modifications which do not substantially affect the activity of the various embodiments of this invention are also provided within the definition of the invention provided herein. Accordingly, the following examples are intended to illustrate but not limit the present invention.

Example I

Detection of Target Nucleic Acids in Iterative Rounds of Fluorescence Detection

This example describes the detection of 12 positive control genes in Hela cells in three rounds of fluorescent detection.

Figure 4A:
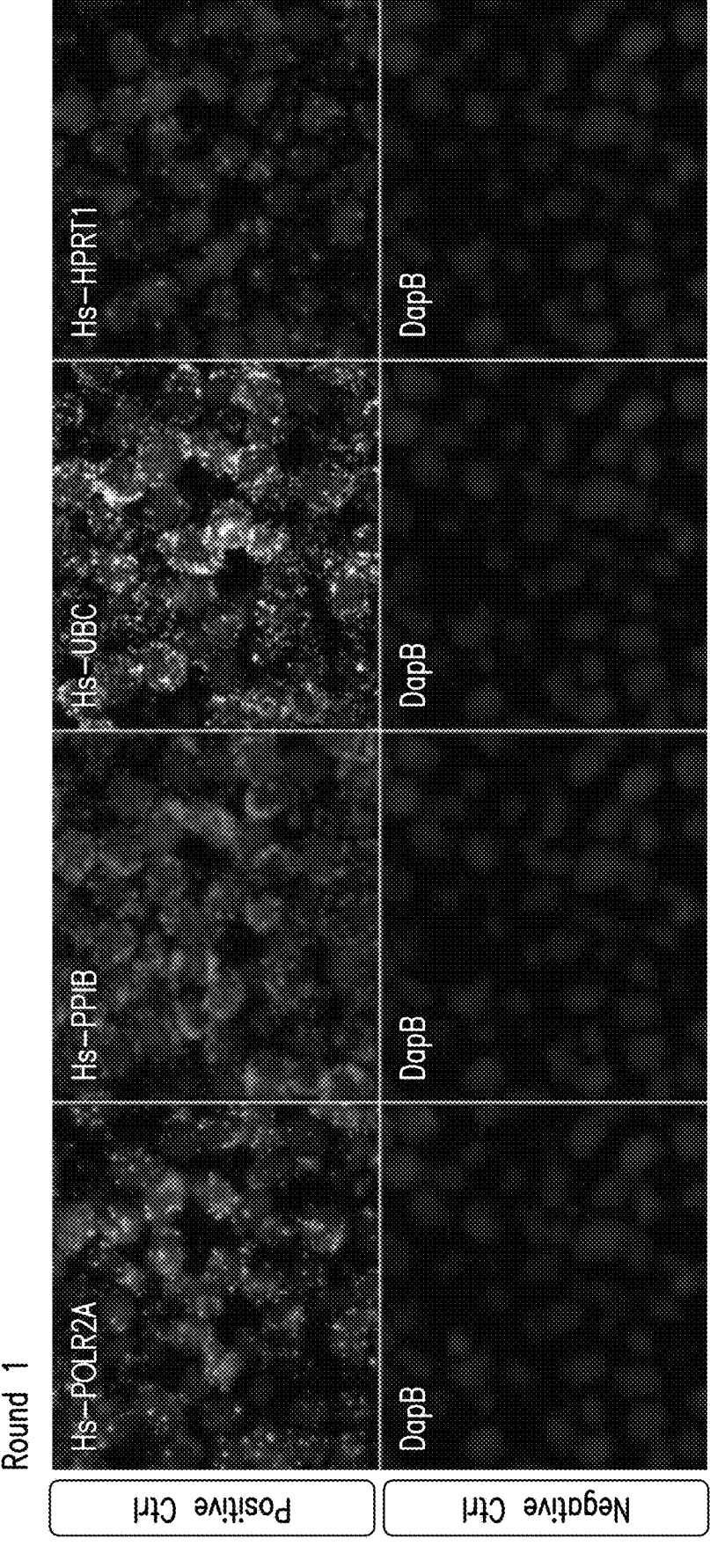
FIGS. 4A-4C show detection of 12 positive control genes in HeLa Cells in three rounds of fluorescent detection. Probe pairs for 12 different targets were hybridized to HeLa cells prepared as formalin-fixed paraffin embedded section, and the hybridization signals were amplified together by successive rounds of hybridization with the preamplifier and amplifier sequences.
Figure 4B:
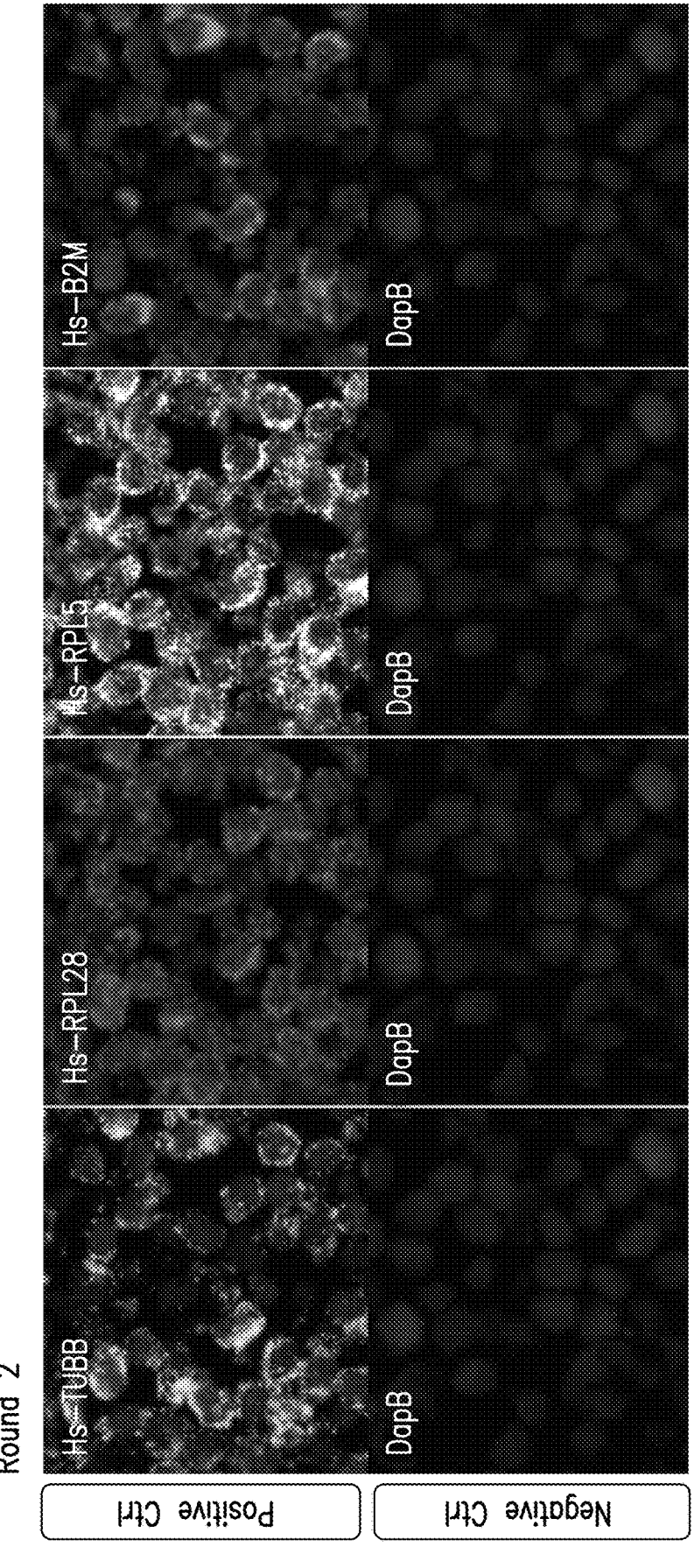
Figure 4C:
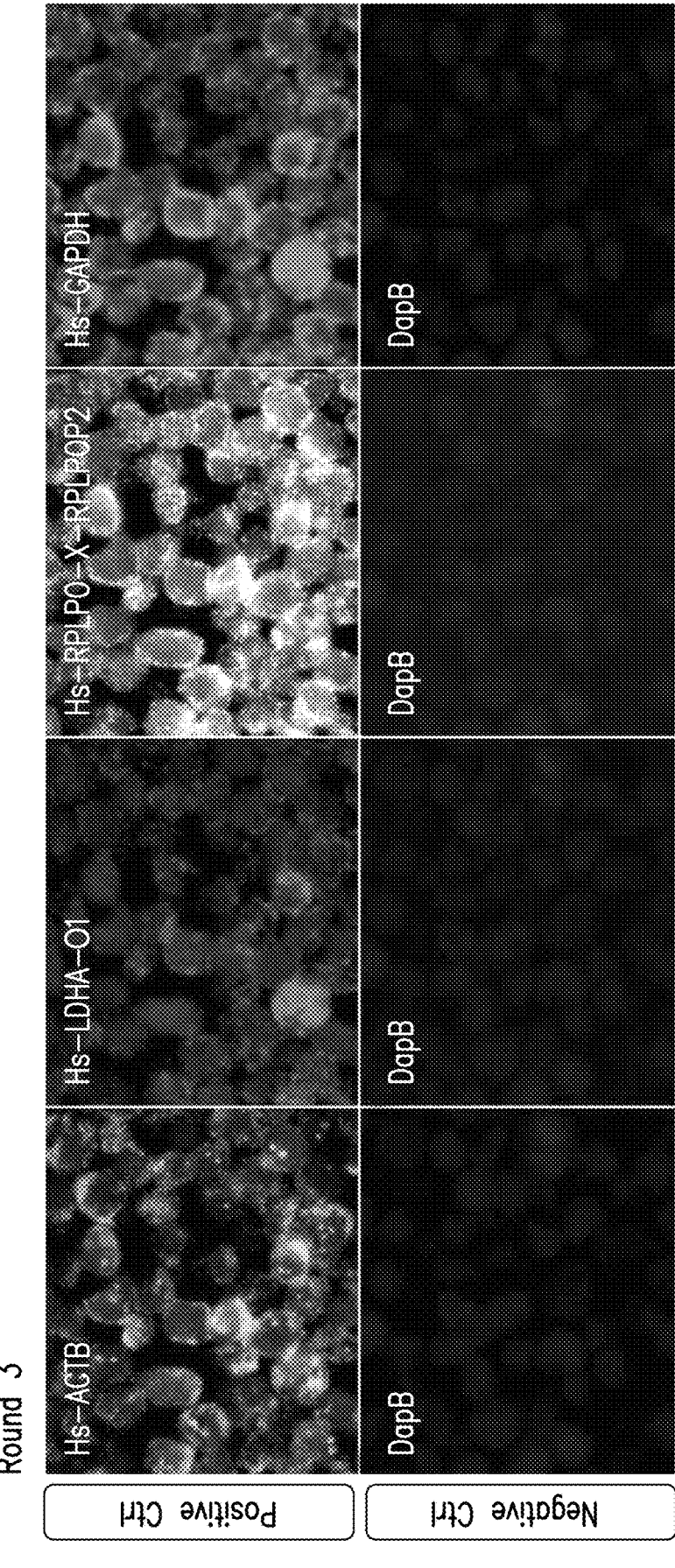

Probe pairs for 12 different targets were hybridized to HeLa cells prepared as formalin-fixed paraffin embedded section, and the hybridization signals were amplified together by successive rounds of hybridization with the preamplifier and amplifier sequences. FIGS. 4A-4C show detection of 12 positive control genes in HeLa Cells in three rounds of fluorescent detection, respectively. Four of the 12 target genes, POLR2A, PPIB, UBC and HPRT1, were detected in round 1 using fluorescent label probes corresponding to the signal amplification systems assigned to these four target probes. POLR2A, PPIB, UBC and HPRT1 were labeled with the fluorophores Alexa 488, ATTO 550, ATTO 647N, and Alexa 750, respectively. On a separate slide, a negative control probe for the bacterial dapB gene was used to assess non-specific background. Nuclei were stained with DAPI (blue). FIG. 4A shows detection of the first round of visualization labels bound to the target nucleic acids. After cleaving the fluorophores off of the label probes from the first round, the second set of label probes were hybridized to detect TUBB, RPL28, RPL5 and B2M using the fluorophores Alexa 488, ATTO 550, ATTO 647N, and Alexa 750, respectively (see FIG. 4B). After cleaving the fluorophores off of the label probes from the second round, the third set of label probes were hybridized to detect ACTB, LDHA, RPLP0 and GAPDH using the fluorophores Alexa 488, ATTO 550, ATTO 647N, and Alexa 750, respectively (see FIG. 4C).

These results demonstrate that iterative rounds of labeling, detection and cleavage can be used to detect multiple target nucleic acids.

Example II

Detection of Target Nucleic Acids in Iterative Rounds of Fluorescence Detection

This example describes detection and image registration of neuronal markers in fresh frozen mouse brain.

Figure 5:
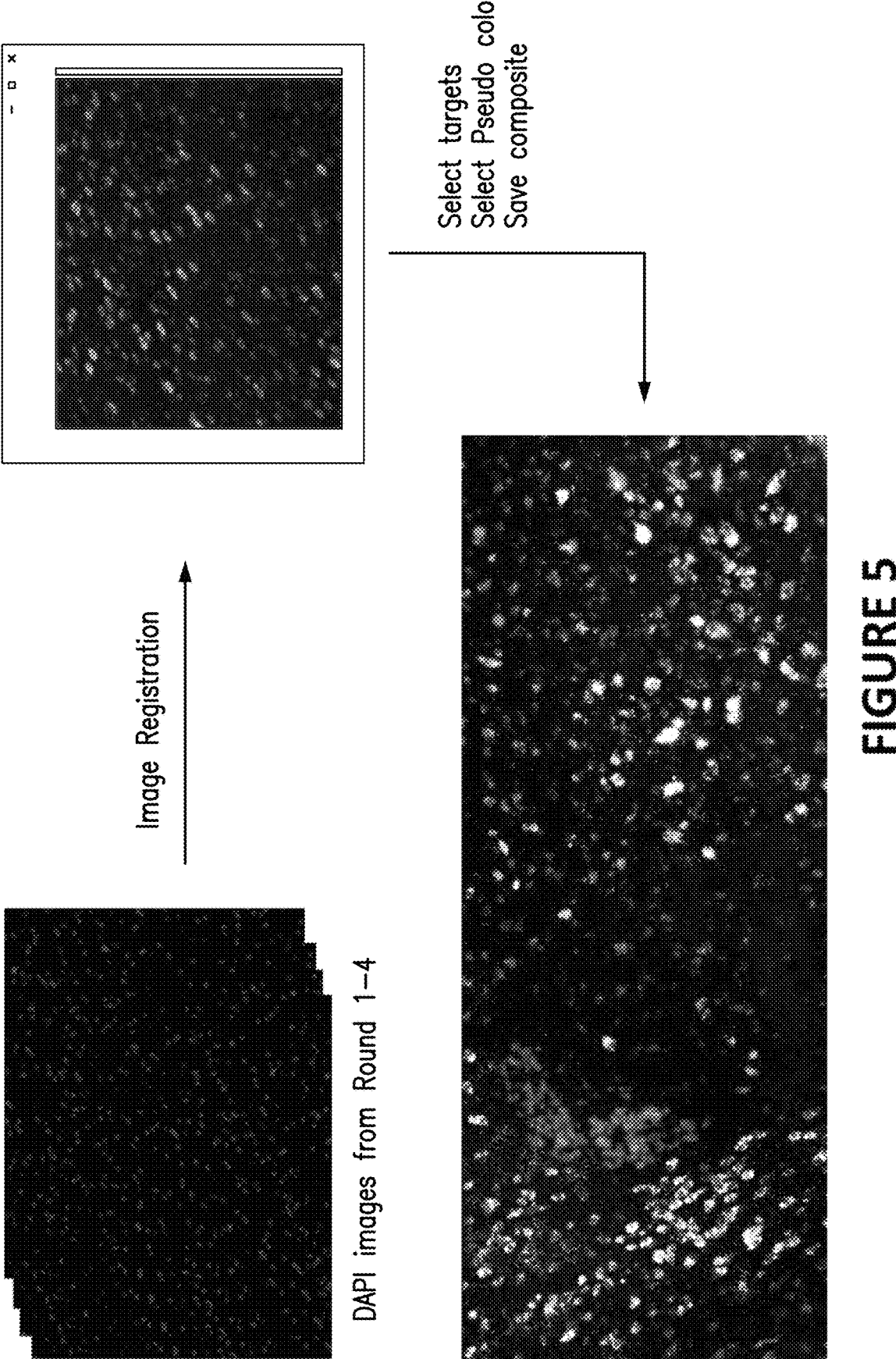
FIG. 5 shows detection and image registration of neuronal markers in fresh frozen mouse brain. Three rounds of label probe hybridization were performed to detect 5-hydroxytryptamine (serotonin) receptor 7 (Htr7), protocadherin 8 (Pcdh8), Meis homeobox 1 (Meis1), tyrosine hydroxylase (Th), crystallin, mu (Crym), synaptoporin (Synpr), dopamine receptor D1 (Drd1a), cannabinoid receptor 1 (brain) (Cnr1), wolframin ER transmembrane glycoprotein (Wfs1), dopamine receptor D2 (Drd2), and calbindin 1 (Calb1) using Alexa 488, ATTO 550, ATTO 647N and Alexa 750 fluorophores, followed by immunofluorescence detection with anti-NeuN (encoded by RNA binding protein, fox-1 homolog (*C. elegans*) 3) antibody using ATTO 550, resulting in a set of four images which were then registered by using image analysis software to superimpose the 12 target signals on the same individual cells.

Fresh frozen mouse brain 10 μM sections were prepared using a standard tissue processing method. Probe pairs for 11 different targets were hybridized to the mouse brain section, and the hybridization signals were amplified together by successive rounds of hybridization with the preamplifier and amplifier sequences. Three rounds of label probe hybridization were performed to detect Htr7, Pcdh8, Meis1, Th, Crym, Synpr, Drd1a, Cnr1, Wfs1, Drd2, Calb1 using Alexa 488, ATTO 550, ATTO 647 and Alexa 750 fluorophores. Immunofluorescent detection with anti-NeuN antibody was performed using ATTO 550. Nuclei were stained with DAPI. DAPI images from each round of detection were used to register (superimpose) the images from the four rounds using image registration software (Advanced Cell Diagnostics). Registered images were overlayed by selecting pseudo colors for each target using the same software, and overlayed images were exported in Tiff. Twelve target signals on the same individual cells were revealed in this manner. Representative overlayed images are shown in FIG. 5. These results demonstrate that iterative rounds of labeling, detection and cleavage can be used to detect multiple target nucleic acids and that the multiple rounds of detection of target nucleic acids can be superimposed to reveal expression of all of the target nucleic acids and a protein in the sample.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of detecting a plurality of target nucleic acids comprising:

(A) contacting a sample comprising a cell comprising a plurality of nucleic acids with a plurality of target probe sets, wherein each target probe set comprises a pair of target probes that specifically hybridize to a target nucleic acid;

(B) contacting the sample with a set of pre-amplifiers, wherein the set of pre-amplifiers comprises a plurality of pre-amplifiers, wherein the plurality of pre-amplifiers comprises a pre-amplifier specific for each target probe set, wherein each pre-amplifier comprises binding sites for the pair of target probes of one of the target probe sets and a plurality of binding sites for an amplifier;

(C) contacting the sample with a set of amplifiers, wherein the set of amplifiers comprises a plurality of subsets of amplifiers specific for each pre-amplifier, wherein each subset of amplifiers comprises a plurality of amplifiers, wherein the amplifiers of a subset of amplifiers comprise a binding site for one of the pre-amplifiers specific for a target probe set and a plurality of binding sites for a label probe; wherein the plurality of target probe sets, the set of pre-amplifiers, and the set of amplifiers are hybridized simultaneously to the plurality of target nucleic acids;

(D) contacting the sample with a first set of label probes, wherein the first set of label probes comprises a plurality of first subsets of label probes, wherein each subset of label probes is specific for the amplifiers of one of the subsets of amplifiers, wherein each subset of label probes comprises a plurality of label probes, wherein the label probes in each of the subsets of label probes comprise a label and a binding site for the amplifiers of one of the subsets of amplifiers, wherein the labels in each first subset of label probes are distinguishable between the first subsets of label probes and wherein the labels are cleavable, and wherein the first set of label probes specifically label a first subset of target nucleic acids hybridized to the plurality of target probe sets;

(E) detecting the label probes of the first set of label probes bound to the target nucleic acids, thereby detecting the first subset of target nucleic acids;

(F) cleaving the labels from the first set of label probes bound to the first subset of target nucleic acids;

(G) contacting the sample with a second set of label probes, wherein the second set of label probes comprises a plurality of second subsets of label probes, wherein each subset of label probes is specific for the amplifiers of one of the subsets of amplifiers, wherein the second subsets of label probes are specific for amplifiers of different subsets of amplifiers than the first subsets of label probes, wherein each subset of label probes comprises a plurality of label probes, wherein the label probes of each of the subsets of label probes comprise a label and a binding site for the amplifiers of one of the subsets of amplifiers, wherein the labels in each second subset of label probes are distinguishable between the second subsets of label probes and wherein the labels are cleavable, and wherein the second set of label probes specifically label a second subset of target nucleic acids hybridized to the plurality of target probe sets that is different than the first subset of target nucleic acids; and (H) detecting the label probes of the second set of label probes bound to the second subset of target nucleic acids, thereby detecting the second subset of target nucleic acids.

2. The method of claim 1, wherein the method further comprises:

(I) cleaving the labels from the second set of label probes bound to the second set of target nucleic acids;

(J) contacting the sample with a third set of label probes, wherein the third set of label probes comprises a plurality of third subsets of label probes, wherein each subset of label probes is specific for the amplifiers of one of the subsets of amplifiers, wherein the third subsets of label probes are specific for amplifiers of different subsets of amplifiers than the first and second subsets of label probes, wherein each subset of label probes comprises a plurality of label probes, wherein the label probes of each of the subsets of label probes comprise a label and a binding site for the amplifiers of one of the subsets of amplifiers, wherein the labels in each third subset of label probes are distinguishable between the third subsets of label probes and wherein the labels are cleavable, and wherein the third set of label probes specifically label a third subset of target nucleic acids hybridized to the plurality of target probe sets that is different than the first and second subsets of target nucleic acids; and (K) detecting the label probes of the third set of label probes bound to the third subset of target nucleic acids, thereby detecting the third subset of target nucleic acids.

3. The method of claim 2, comprising repeating steps (I) through (K).

4. The method of claim 1, wherein each target probe set comprises two or more pairs of target probes that specifically hybridize to the same target nucleic acid.

5. The method of claim 1, wherein the target nucleic acids are independently DNA or RNA.

6. The method of claim 5, wherein the target nucleic acids that are RNA are independently selected from the group consisting of messenger RNA (mRNA), micro RNA (miRNA), ribosomal RNA (rRNA), mitochondrial RNA, and non-coding RNA.

7. The method of claim 1, wherein the sample is a tissue specimen or is derived from a tissue specimen.

8. The method of claim 1, wherein the sample is a blood sample or is derived from a blood sample.

9. The method of claim 1, wherein the sample is a cytological sample or is derived from a cytological sample.

* * * * *